US007135561B2

(12) United States Patent
Elbers et al.

(10) Patent No.: US 7,135,561 B2
(45) Date of Patent: Nov. 14, 2006

(54) INFECTIOUS BOVINE VIRAL DIARRHEA VIRUS CLONE

(75) Inventors: Knut Elbers, Gau Algesheim (DE); Christiane Meyer, Muenster (DE); Martina Von Freyburg, Tuebingen (DE); Gregor Meyers, Walddorfhaeslach (DE)

(73) Assignee: Boehringer Ingelheim Vetmedica GmbH, St. Joseph, MO (US)

( * ) Notice: Subject to any disclaimer, the term of this patent is extended or adjusted under 35 U.S.C. 154(b) by 249 days.

(21) Appl. No.: 10/236,542

(22) Filed: Sep. 6, 2002

(65) Prior Publication Data

US 2004/0038198 A1  Feb. 26, 2004

Related U.S. Application Data

(60) Provisional application No. 60/322,974, filed on Sep. 18, 2001.

(30) Foreign Application Priority Data

Sep. 6, 2001  (DE) ................. 101 43 813

(51) Int. Cl.
C07H 21/04 (2006.01)
A61K 39/12 (2006.01)
A01N 63/00 (2006.01)
C12N 15/09 (2006.01)
C12Q 1/70 (2006.01)

(52) U.S. Cl. ............... 536/23.72; 536/23.72; 424/218.1; 424/93.6; 435/320.1

(58) Field of Classification Search .......... None
See application file for complete search history.

(56) References Cited

U.S. PATENT DOCUMENTS 6,001,613 A  12/1999  Donis et al. ........... 435/91.4

FOREIGN PATENT DOCUMENTS

| EP | 1013757 A2 | 6/2000 |
|---|---|---|
| WO | WO-9964604 A2 | 12/1999 |
| WO | WO 01/39801 | 6/2001 |

OTHER PUBLICATIONS

Sequence alignment provided of SEQ ID No. 1 with GenEmbl database accession No. BVU18059, submitted Dec. 7, 1995.*
Collett, Marc S. et al; Proteins Encoded by Bovine Viral Diarrhea Virus: The Genomic Organization of a Pestivirus; Virology: (1988) 200-208; vol. 165.
Meyer, Christiane; Recovery of Virulent and RNase-Negative Attenuated Type 2 Bovine Viral Diarrhea Viruses from Infectious cDNA Clones; (2002) 8494-8503; vol. 76; No. 16.
Meyers, Gregor et al; Mutations Abrogating the RNase Activity in Glycoprotein Erns of the Pestivirus Classical Swine Fever Virus Lead to Virus Attenuation; Journal of Virology (1999) 10224-10235; vol. 73; No. 12.
Tratschin, Jon-Duri et al; Classical Swine Fever Virus Leader Proteinase NPRO Is Not Required for Viral Replication in Cell Culture; Journal of Virology (1998) 7681-7684; vol. 72; No. 9.
Moser, Christian et al; A Recombinant Classical Swine Fever Virus Stably Expresses a Marker Gene; Journal of Virology (1998) 5318-5322; vol. 72; No. 6.
Becher, Paul et al; Phylogenic analysis of pestiviruses from domestic and wild ruminants; Journal of eneral Virology (1997) 1357-1366; vol. 78.
Tijssen, P. et al; Immunodominant E2 (gp53) Sequences of Highly Virulent Bovine Viral Diahrrhea Group II Viruses Indicate a Close Resemblence to a Subgroup of Border Disease Viruses; Virology (1996) 356-361; vol. 217.
Schaefer, Brian; Revolutions in Rapid Amplification of cDNA Ends: New Strategies for Polymerase Chain reaction Cloning of Full-Length cDNA Ends; analytical Biochemistry; (1995) 255-273; vol. 227.
Avalos-Ramirez, Ramiro et al; Evidence for the Presence of Two Novel Pestivirus Species: Virology (2001) 456-465 vol. 286.
Stoffregen, B. et al; Morphologic lesions in type 2 BVDV Infections experimentally induced by strain BVDV2-1373 recovered from a field case: Veterinary Microbiology (2000) 157-162: vol. 77.
van Gennip, H.G.P. et al; Recovery of infectious clasiical swine fever virus (CSFV) from full-length genomic cDNA clones by a swine kidney cell line expressing bacteriophage T7 RNA polymerase: Journal of Virological Methods (1999) 117-128; vol. 78.
Odeon, A. C. et al; Experimental infection of calves with bovine viral diarrhea virus genotype II (NY-93): J Vet Diagn Invest 11: 221-228.
Racaniello, V.R. et al; Cloned Poliovirus Complimentary DNA Is Infections in Mammalian Cells; Science, 1981;214:916-919.
Carman, S. et al: Severe acute bovine viral diarrhea in Ontario, 1993-1995; J. Vet. Diagn Invest., 1998, 10:27-35.
The copending applications cited below are brought to the Examiner's attention but are not conceded to be prior art.
Elbers, K. et al: Safe Attenuated Bovine Viral Diarrhea Viruses For Use In Pregnant Cows, U.S. Appl. No. 09/706,649, filed Nov. 6, 2000.
Meyers, G.: Attenuated pestiviruses, U.S. Appl. No. 09/325,542, filed Apr. 6, 1999.
Julia F. Ridpath et al; The Genomic Sequence of a Virulent Bovine Viral Diarrhea Virus (BVDV) from the Type 2 Genotype: Detection of a Large Genomic Insertion in a Noncytopathic BVDV; Virology (1995) vol. 212 pp. 39-46; Virology Cattle Research National Animal Disease Center, Iowa.

(Continued)

Primary Examiner—Bruce R. Campell
Assistant Examiner—Benjamin P. Blumel
(74) Attorney, Agent, or Firm—Michael P. Morris; Mary-Ellen M. Devlin

(57) ABSTRACT

The invention belongs to the field of animal health and in particular Bovine Viral Diarrhea Virus (BVDV). The invention provides infectious BVDV clones and methods to produce said BVDV clones. The invention further relates to methods of attenuating said clones, attenuated BVDV clones and vaccines comprising said attenuated clones.

5 Claims, 8 Drawing Sheets

OTHER PUBLICATIONS

Christina L. Topliff et al; Virulence Markers in the 5' Untranslated Region of Genotype 2 Bovine Viral Diarrhea Virus Isolates; Virology (1998) vol. 250 p. 164-172; Agricultural Research Division University of Nebraska.

Beate M. Kummerer et al; Correlation between Point Mutations in NS2 and the Viability and Cytopathogenicity of Bovine Viral Diarrhea Virus Strain Oregon Analyzed with an Infections cDNA Clone: Journal of Virology Jan. 2000 vol. 74 No. 1 p. 390-400; American Society for Microbiology.

Gregor Meyers et al; Recovery of Cytopathogenic and Noncytopathogenic Bovine Viral Diarrhea Viruses from cDNA Constructs; Journal of Virology Dec. 1996 vol. 70 No. 12 p. 8606-8613; American Society of Microbiology.

Ventzislav B. Vassilev et al; Authentic and Chimeric Full-Length Genomic cDNA Clones of Bovine Viral Diarrhea Virus that Yield Infectious Transcriptst; Journal of Virology Jan. 1997 vol. 71 No. 1 p. 471-478: American Society for Microbiology.

Database Accession No. AF145967; XP002251610.

Copy of International Search Report for Reference PCT/EP 02/09925.

Constans, Aileen; Recent Developments in RT-PCR Technology Move Reverse Transcription in the right direction; The Scientist-Reverse Psychology 14[17]; 29, Sep. 4, 2000 pp. 1-4.

van der Poel, W.H.M.; Experimental Reproduction of Respiratory Disease in Calves with Non-Cell-Culture-Passaged Bovine respiratory Synctial Virus, The Veterinary Quarterly, vol. 18, No. 3, Sep. 1996—XP 009041333, pp. 81-86.

* cited by examiner

FIGURE 3

INFECTIOUS BOVINE VIRAL DIARRHEA VIRUS CLONE

RELATED APPLICATION

This application claims priority benefit of U.S. provisional application Ser. No. 60/322,974, filed Sep. 18, 2001.

BACKGROUND OF THE INVENTION

The invention belongs to the field of animal health and in particular Bovine Viral Diarrhea Virus (BVDV). The invention provides infectious BVDV clones and methods to produce said BVDV clones. The invention further relates to methods of attenuating said clones, attenuated BVDV clones and vaccines comprising said attenuated clones.

Bovine Viral Diarrhea Virus (BVDV) is the causative agent of BVD and mucosal disease in cattle (Baker, J. C., 1987, J. Am. Vet. Med. Assoc. 190:1449–1458; Moennig, V. and Plagemann, J., 1992; Adv. Virus Res. 41:53–91; Thiel, H. J. et al., 1996, Fields Virology 1059–1073). Fetal infection during pregnancy can result in the resorption of the fetus, abortions, as well as birth of immunotolerant calves which are persistently infected with BVDV. These calves lack or have very low neutralizing antibody titers and are continuously shedding high amounts of virus. Next to acutely infected cattle these calves are the major source for virus spreading and are therefore of prime importance in the epidemiology of this disease. The major economical impact of BVD results from high abortion rates, stillbirths, fetal resorption, mummification, congenital malformations, and birth of weak and undersized calves. For a detailed review of the pathogenesis, hereby refer to the article of Moennig, V. and Liess, B. of 1995, Virus, 11(3):477–487.

Two major antigenic groups of BVDV (type 1 and 2) have been described (Becher, P. et al. 1999, Virology 262:64–71) which display limited cross neutralizing antibody reactions (Ridpath, J. F., et al. 1994, Virology 205:66–74).

Present vaccines for the prevention and treatment of BVDV infections still have drawbacks (Oirschot, J. T., et al. 1999, Veterinary Microbiology, 64:169–183). Vaccines against the classical BVDV type 1 provide only partial protection from type 2 infection, and vaccinated dams may produce calves that are persistently infected with virulent BVDV type 2 (Bolin, S. R., et al., 1991, Am. J. Vet. Res. 52:1033–1037; Ridpath, J. F., et al., 1994, Virology 205: 66–74). This problem is probably due to the great antigenic diversity between type 1 and type 2 strains which is most pronounced in the glycoprotein E2, the major antigen (Tijssen, P., et al., 1996, Virology 217:356–361). most monoclonal antibodies against type 1 strains fail to bind to type 2 viruses (Ridpath, J. F., et al., 1994, Virology 205:66–74).

Killed vaccines (inactivated whole virus) or subunit vaccines (conventionally purified or heterologously expressed purified viral proteins) are most often inferior to live vaccines in their efficacy to produce a full protective immune response even in the presence of adjuvants.

Live BVDV vaccines, although attenuated, are most often associated with safety problems. As mentioned above, they cross the placenta of pregnant cows and lead to clinical manifestations in the fetus and/or the induction of persistently infected calves. Therefore, they cannot be applied to breeding herds that contain pregnant cows. Pregnant cows have to be kept separate from vaccinated cattle to protect fetuses and must not be vaccinated themselves. Furthermore, revertants of attenuated live BVDV pose a serious threat to cattle. For conventionally derived attenuated viruses wherein the attenuation is achieved by conventional multiple passaging, the molecular origin as well as the genetic stability of the attenuation remains unknown and reversion to the virulent wild-type is unpredictable.

Live vaccines with defined mutations as a basis for attenuation would overcome the disadvantages of the present generation of attenuated vaccines. A further advantage of said attenuating mutations lies in their defined molecular uniqueness which can be used as a distinctive label for the attenuated *pestivirus* to distinguish it from *pestiviruses* from the field.

In the art, BVDV of defined genetic identity which closely resemble wild-type viruses are hardly known, in particular not for type 2 BVDV. In the art, there was a long lasting need for methods to generate such BVDV. Therefore, the technical problem underlying this invention was to provide a BVDV, in particular a BVDV type 2, of defined genetic identity.

SUMMARY OF THE INVENTION

The invention relates to a DNA molecule comprising a nucleotide sequence complimentary to a BVDV RNA, wherein said RNA induces the generation of infectious BVDV particles in susceptible host cells. In an embodiment, administration of a dose of $6 \times 10^6 TCID_{50}$ of the infectious BVDV particles to a calf induces viraemia and leukopenia in said calf for a period of at least one day and induces diarrhea or pyraemia for a period of at least one day. In another embodiment, said infectious BVDV particles have authentical virulence as compared to a wild-type BVDV isolate from which said DNA molecule was derived. In another embodiment, administration of a dose of $6 \times 10^6 TCID_{50}$ per calf of said infectious BVDV particles to BVDV naive calves is lethal for at least 30% of said calves within 21 days.

In another embodiment, said BVDV particles have a virulence of at least 90% of BVDV particles comprising an RNA, wherein the nucleotide sequence of said RNA is complementary to SEQ ID NO:1. In another embodiment, the DNA molecules of the invention comprise a nucleotide sequence complementary to a BVDV RNA, whereon the nucleotide sequence of said BVDV RNA comprises a sequence complementary to SEQ ID NO:1. In another embodiment, the DNA molecule of the invention comprises SEQ ID NO:1.

The invention also relates to an infectious BVDV clone, i.e., a vector comprising a DNA molecule of the invention or a host cell strain comprising said vector. In a preferred embodiment, the invectious BVDV clone is a BVDV type 2 clone.

The invention also relates to a BVDV particle generated by transcription of a DNA molecule or a BVDV clone of the invention into RNA, wherein a cell is transfected with said RNA such that BVDV particles are produced by said cell.

The invention also relates to fragments, derivatives and variants of the molecules of the invention.

The invention also relates to a method for producing a BVDV type 2 clone comprising: (a) isolating a wild-type BVDV type 2 strain; (b) passaging said wild-type BVDV type 2 strain in cell culture; (c) infecting a bovine with said passaged wild-type BVDV type 2 strain of step (b); (d) isolating a BVDV type 2 strain from said infected bovine of step (c); (e) passaging said isolated BVDV type 2 strain of step (d) in cell culture no more than two times; (f) transcribing the passaged BVDV type 2 strain of step (c) by reverse transcription; and (g) cloning the transcribed BVDV type 2 strain of step (f). The invention also relates to a BVDV type 2 clone or BVDV strain obtained by methods of the invention. In another embodiment, a BVDV type 2 particle is obtained by: (1) transcribing an infectious DNA clone of the invention into RNA; (b) introducing said RNA into a cell such that a BVDV type 2 particle is produced; and (c) collecting said BVDV type 2 particle.

The invention also relates to a method for producing an infectious BVDV clone from a wild-type BVDV isolate comprising: (a) isolating viral particles from an infected bovine; (b) passaging said viral particles not more than two times in cell culture; (c) preparing RNA from said passaged viral particles of step (b); (d) transcribing said RNA by reverse transcription to generate full-length cDNA, wherein said reverse transcription is performed at an elevated temperature and using a thermostable enzyme such that secondary structures of said RNA are broken or reduced; and (e) incorporation of said cDNA into a vector or DNA virus capable of transcribing said cDNA into RNA upon infection of a cell; wherein said infectious BVDV clone is complementary to an RNA having authentic virulence compared to said wild-type BVDV isolate. In an embodiment, said infectious BVDV clone is complementary to an RNA having a virulence of at least 90% of said wild-type isolate.

The invention also relates to a method for producing an infectious BVDV clone from a wild-type BVDV isolate comprising: (a) isolating RNA from cells from an infected bovine; (b) transcribing said RNA by reverse transcription to generate full-length cDNA, wherein said reverse transcription is performed at an elevated temperature and using a thermostable enzyme, such that secondary structures of said RNA are broken or reduced; and (c) incorporating said BVDV cDNA into a vector or DNA virus capable of transcribing said cDNA into RNA upon infection of a cell; wherein said BVDV clone is complementary to an RNA having authentical virulence compared to said wild-type BVDV isolate. In an embodiment, RNA is isolated from a cell of an infected bovine during viraemia. In another embodiment, RNA is isolated from an infected bovine after killing said bovine.

In an embodiment, full-length BVDV cDNA is assembled from cDNA fragments after reverse transcription of RNA, preferably, overlapping cDNA fragements.

The invention also relates to a method of attenuation of a BVDV strain, comprising: (a) introducing one or more mutations into a DNA molecule of the invention, or into a infectious BVDV clone of the invention; (b) introducing the mutated DNA into susceptible host cells wherein said DNA is transcribed into RNA or introducing an RNA transcribed from said DNA into said cells; and (c) collecting viral particles produced by these cells; wherein said mutation or mutations results in attenuation. Preferably, the mutation or mutations is a nucleotide substitution, deletion, insertion, addition, or combination thereof.

The invention encompasses BVDV clones wherein the RNase activity residing in glycoprotein En is inactivated. Preferably, said RNase activity is inactivated by deletion and/or other mutation such as substitution. Preferably, said deletions and/or other mutations are located at the amino acids at position 295 to 307 and/or position 338 to 357.

Preferably, a method of attenuation of the invention comprises: (a) deletion of all or part of the glycoprotein $E^{ms}$; and/or (b) deletion or substitution of histidine at position 300 of SEQ ID NO:1; and/or (c) deletion or substitution of histidine at position 349 of SEQ ID NO:1.

Most preferably, a method for the attenuation of BVDV, comprises mutation of a BVDV clone according to the invention at histidine position 300 and/or position 349 wherein the coding triplet in the nucleotide sequence is deleted or substituted.

In another embodiment, a method for the attenuation of BVDV according to the invention, comprises substituting the codon encoding histidine 300 for a codon encoding leucine.

Yet another important embodiment is a method for the attenuation of BVDV according to the invention, wherein the codon encoding histidine 349 is deleted.

Another important embodiment of the invention is a vaccine comprising an attenuated BVDV clone or strain according to the invention, optionally in combination with a pharmaceutically acceptable carrier or excipient.

The invention further relates to the use of an attenuated BVDV clone or strain according to the invention in the manufacture of a vaccine for the prophylaxis and/or treatment of BVDV infections.

Preferably, a vaccine of the invention refers to a vaccine as defined above, wherein one immunologically active component is a live BVDV, wherein the RNase activity in its protein $E^{ms}$ is inactivated.

Preferably, a vaccine according to the invention comprises an attenuated BVD virus type 1 according to the invention combined with an attenuated BVD virus type 2 according to the invention or any other antigenetic group and a pharmaceutically acceptable carrier or excipient. Said vaccine may be administered as a combined vaccine. Most preferably, said attenuated BVD virus type 1 according to the invention may be administered first, followed by an administration of an attenuated BVD virus type 2 according to the invention three to four weeks later.

Preferably, a vaccine according to the invention comprises an attenuated BVD virus type 1 according to the invention wherein the RNase activity in its protein $E^{ms}$ is inactivated, combined with an attenuated BVD virus type 2 according to the invention wherein the RNase activity in its protein $E^{ms}$ is inactivated, or any other antigenetic group wherein the RNase activity in its protein $E^{ms}$ is inactivated, and a pharmaceutically acceptable carrier or excipient. Said vaccine may be administered as a combined vaccine. Most preferably, said attenuated BVD virus type 1 according to the invention as described supra may be administered first, followed by an administration of an attenuated BVD virus type 2 according to the invention as described supra three to four weeks later.

The invention preferably relates to a method of treating a BVDV-infected bovine animal with an attenuated BVDV according to the invention as described supra, wherein said attenuated BVDV or the vaccine composition as disclosed supra is administered to the bovine animal in need thereof at a suitable dose as known to the skilled person and the reduction of BVDV symptoms such as viremia and leukopenia and/or pyrexia and/or diarrhea is monitored. Said treatment preferably may be repeated.

DESCRIPTION OF THE FIGURES

FIG. 3: Growth curves of the recombinant virus XIKE-A and the $E^{rns}$ mutants XIKE-B (H349Δ) and XIKE-C (H300L). MDBK cells were infected with the viruses at an m.o.i of 0.1 and harvested by freezing and thawing at the indicated time points. Titers were determined after infection of new MDBK cells by immunofluorescence staining 72 h p.i.

DESCRIPTION OF THE INVENTION

Figure 1:
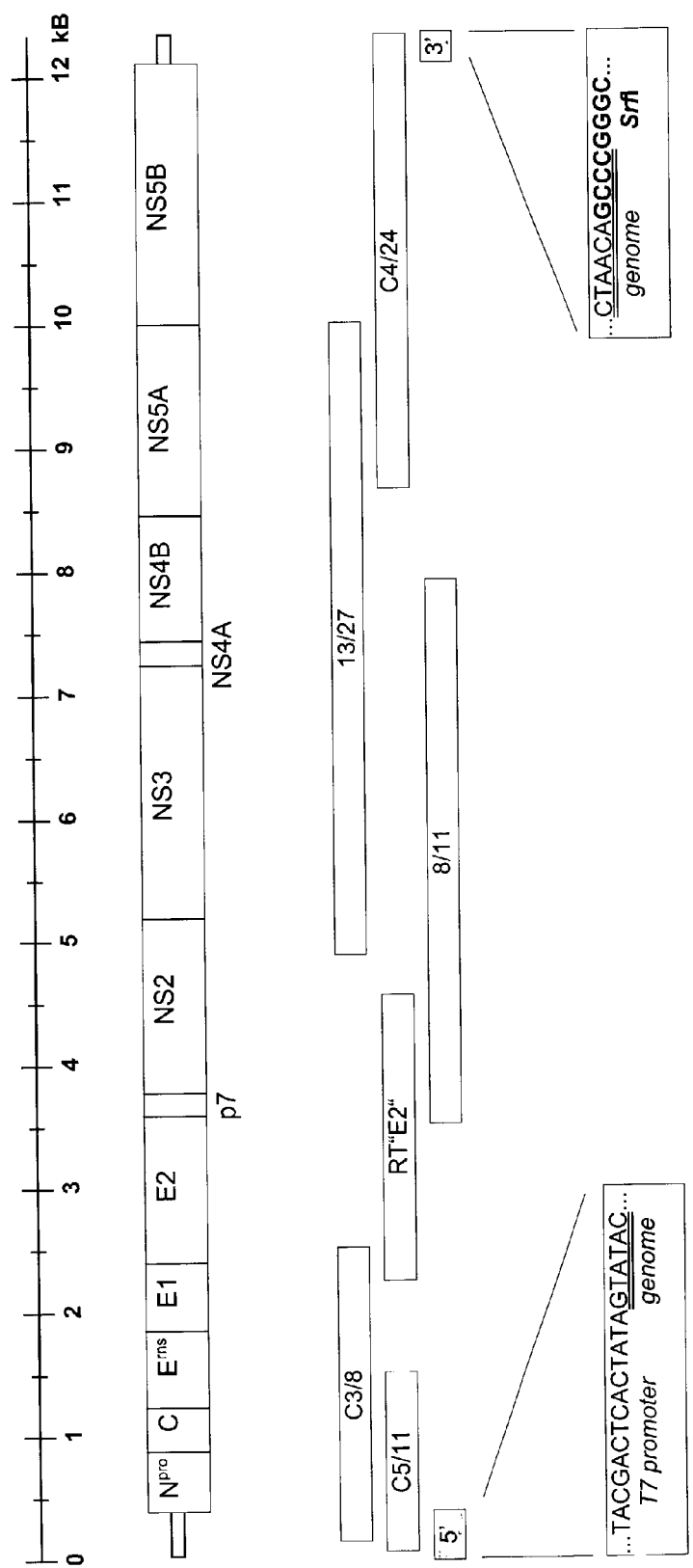
FIG. 1: Construction of the infectious cDNA clone. The upper part sketches a BVDV genome (kB) and the encoded polyprotein. The middle part shows the cDNA clones (white), the RT-PCR product (light grey) and the PCR products (dark grey) used for engineering the infectious cDNA clone. The lower part depicts the ends of the genomic cDNA sequences (underlined) and the sequences added at the 5' and 3' ends for in vitro transcription.

Definitions of Terms Used in the Description:

Before the embodiments of the present invention it must be noted that as used herein and in the appended claims, the singular forms "a", "an", and "the" include plural reference unless the context clearly dictates otherwise. Thus, for example, reference to "a BVDV virus" includes a plurality of such BVDV viruses, reference to "the cell" is a reference to one or more cells and equivalents thereof known to those skilled in the art, and so forth. Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated by reference. Nothing herein is to be construed as an admission that the invention is not entitled to antedate such disclosure by virtue of prior invention.

The term "BVDV" as used herein refers to all viruses belonging to species BVDV 1 and BVDV 2 in the genus *pestivirus* within the family Flaviviridae (Becher, P., et al. 1999, Virology 262:64–71).

The more classical BVDV type 1 strains and the more recently recognized BVDV type 2 strains display some limited but distinctive differences in nucleotide and amino acid sequences.

A "clone" is a DNA vector or host cell strain into which such vector has been introduced. Preferably, the DNA vector is a plasmid.

An "infectious clone" is a DNA vector with the capability to serve as a template for transcription into an RNA that induces the generation of the virus when introduced into susceptible cells. Preferably the RNA is produced by in vitro transcription and introduced into the cells by transfection technologies known to the skilled person.

"BVDV particles" or "viral particles" as used herein relate to BVD viruses generated from "infectious clones" via RNA, that will induce production of said BVDV particles when introduced into susceptible cells.

The term "attenuated BVDV particles" or "attenuated viral particles" as used herein relates to BVDV particles attenuated by a method according to the invention (see infra).

"Infectivity" is the capability of a virus or viral particle to induce a certain number of plaques in a plaque test or a certain $TCID_{50}$ score in an endpoint test.

A full-length RNA is an RNA comprising at least 98% of the sequence of an RNA occurring in a wild-type isolate. A full-length complementary DNA is a DNA comprising a sequence complementary to at least 98% of an RNA occurring in a wild-type isolate.

As used herein, "calf" relates to a bovine animal of six months of age or less. Virulence: "Authentical virulence" as used herein means that there is no statistically significant difference between the virulence of infectious BVDV particles according to the invention and wild-type BVDV isolates from which said DNA molecules containing a nucleotide sequence complementary to a BVDV RNA, preferably a type 2 RNA has been derived, for at least one predominant clinical parameter. Examples of such predominant clinical parameters are diarrhea, pyrexia and/or lethality.

Attenuation: "An attenuated BVDV particle" as used herein means that there is a statistically significant difference between the virulence of attenuated BVDV particles according to the invention, said attenuated BVDV particles being attenuated by a method according to the invention, and wild-type BVDV isolates from which said attenuated BVDV particles have been derived, for the predominant clinical parameters diarrhea, pyrexia and lethality in animals infected with the same dose, preferably $6 \times 10^6 TCID_{50}$. Thus, said attenuated BVDV particles do not cause diarrhea, pyrexia and lethality and thus may be used in a vaccine.

"RACE" as used herein means rapid amplification of cDNA ends and is known as such in the art (Frohman et al, Proc. Natl. Acad. Sci USA 1988, 85: 8998–9002).

"Susceptible cell" as used herein is a cell which can be infected with BVDV or transfected with BVDV RNA, wherein said virus or RNA, when introduced into said susceptible cells, induces the generation of infectious BVDV.

A "fragment" according to the invention is any subunit of a DNA molecule or infectious BVDV clone according to the invention, i.e. any subset, characterized in that it is encoded by a shorter nucleic acid molecule than disclosed which can still be transcribed into RNA.

A "functional variant" of the DNA molecule or infectious BVDV clone according to the invention is a DNA molecule or infectious BVDV clone which possesses a biological activity (either functional or structural) that is substantially similar to the DNA molecule or infectious BVDV clone according to the invention. The term "functional variant" also includes "a fragment", "a functional variant", "variant based on the degenerative nucleic acid code" or "chemical derivative". Such a "functional variant" e.g. may carry one or several nucleic acid exchanges, deletions or insertions. Said exchanges, deletions or insertions may account for 10% of the entire sequence. Said functional variant at least partially retains its biological activity, e.g. function as an infectious clone or a vaccine strain, or even exhibits improved biological activity.

A "variant based on the degenerative nature of the genetic code" is a variant resulting from the fact that a certain amino acid may be encoded by several different nucleotide triplets. Said variant at least partially retains its biological activity, or even exhibits improved biological activity.

A "fusion molecule" may be the DNA molecule or infectious BVDV clone according to the invention fused to e.g. a reporter such as a radiolabel, a chemical molecule such as a fluorescent label or any other molecule known in the art.

As used herein, a "chemical derivative" according to the invention is a DNA molecule or infectious BVDV clone according to the invention chemically modified or containing additional chemical moieties not normally being part of the molecule. Such moieties may improve the molecule's solubility, absorption, biological half life etc.

A molecule is "substantially similar" to another molecule if both molecules have substantially similar nucleotide sequences or biological activity. Thus, provided that two molecules possess a similar activity, they are considered variants as that term is used herein if the nucleotide sequence is not identical, and two molecules which have a similar nucleotide sequence are considered variants as that term is used herein even if their biological activity is not identical.

The term "vaccine" as used herein refers to a pharmaceutical composition comprising at least one immunologically active component that induces an immunological response in an animal and possibly but not necessarily one or more additional components that enhance the immunological activity of said active component. A vaccine may additionally comprise further components typical of pharmaceutical compostions. The immunologically active component of a vaccine may comprise complete virus particles in either their original form or as attenuated particles in a so called modified live vaccine (MLV) or particles inactivated by appropriate methods in a so called killed vaccine (KV). In another form, the immunologically active component of a vaccine may comprise appropriate elements of said organisms (subunit vaccines) whereby these elements are generated either by destroying the whole particle or the growth cultures containing such particles and optionally subsequent purification steps yielding the desired structure(s), or by synthetic processes including an appropriate manipulation by use of a suitable system based on, for example, bacteria, insects, mammalian or other species plus optionally subsequent isolation and purification procedures, or by induction of said synthetic processes in the animal needing a vaccine by direct incorporation of genetic material using suitable pharmaceutical compositions (polynucleotide vaccination). A vaccine may comprise one or simultaneously more than one of the elements described above.

The term "vaccine" as understood herein is a vaccine for veterinary use comprising antigenic substances and is administered for the purpose of inducing a specific and active immunity against a disease provoked by BVDV. The BVDV clone according to the invention confers active immunity that may be transferred passively via maternal antibodies against the immunogens it contains and sometimes also against antigenically related organisms.

Additional components to enhance the immune response are constituents commonly referred to as adjuvants, e.g. aluminium hydroxide, mineral or other oils or ancillary molecules added to the vaccine or generated by the body after the respective induction by such additional components, including but not restricted to interferons, interleukins or growth factors.

A "pharmaceutical composition" essentially consists of one or more ingredients capable of modifying physiological e.g. immunological functions of the organism it is administered to, or of organisms living in or on the organism. The term includes, but is not restricted to antibiotics or antiparasitics, as well as other constituents commonly used to achieve certain other objectives like, but not limited to, processing traits, sterility, stability, feasibility to administer the composition via enteral or parenteral routes such as oral, intranasal, intravenous, intramuscular, subcutaneous, intradermal or other suitable route, tolerance after administration, controlled release properties.

DISCLOSURE OF THE INVENTION

The solution to the above technical problem is achieved by the description and the embodiments characterized in the claims.

The long lasting need in the art has been overcome for a live BVDV (bovine viral diarrhea virus) of defined sequence and specificity correlated to virulence which can be used to generate specific attenuated BVDV for use, for example, in a vaccine. The inventors for the first time provide a method to generate infectious clones and infectious BVDV particles derived thereof of defined genetic identity which at the same time have the pathogenicity closely resembling the wild-type virus.

Furthermore, the inventors for the first time disclose an infectious type 2 clone and infectious type 2 BVDV particles derived thereof. Thirdly, the inventors also disclose a method to generate attenuated BVDV particles with genetic identity which may be attenuated by modification at only one defined genetic marker site. The methods of the invention can be used to disclose a causal link between genome modification and attenuation, which is essential in order to understand the functional mechanism of the attenuation and therefore is helpful in assessing the quality for use as a vaccine.

In a first important embodiment, the invention relates to a DNA molecule containing a nucleotide sequence complementary to a BVDV RNA, wherein said RNA, when introduced into susceptible host cells, induces the generation of infectious BVDV particles:

a) with the capability to induce viraemia and leukopenia in a calf for a period of at least one day and at least one of the following clinical symptoms of the group comprising diarrhea and/or pyrexia lasting at least one day when infected with a dose of $6 \times 10^6 TCID_{50}$; and/or b) with authentical virulence as defined supra as compared to a wild-type BVDV isolate from which such DNA molecule has been derived; and/or c) which are, when BVDV naive calves are infected at a dose of $6 \times 10^6 TCID_{50}$ with such particles, lethal for at least 30% of such calves within a period of 21 days; and/or d) with a virulence of not less than 90% of BVDV particles comprising an RNA with a sequence complementary to SEQ ID NO:1; and/or e) comprising a sequence complementary to SEQ ID NO:1.

Said dose of $6\times10^6 TCID_{50}$ of step a) is preferably administered as $2\times10^6$ i.m. (gluteal muscle), $2\times10^6$ intranaseally, and $2\times10^6$ subcutaneously (over scapula) to obtain a total dose of $6\times10^6$. Said clinical symptoms of step a) preferably should be observed in at least two thirds of all infected animals. Said leukopenia of step a) preferably shall be at least a 35% reduction below baseline on at least two consecutive days, wherein "baseline" relates to the average values of all animals 10 days before infection. Diarrhea is a typical symptom of infection with BVDV.

Preferably, in a DNA molecule according to the invention as described supra the pyrexia of step a) is at least 40° C.

In a second important embodiment the invention relates to an infectious BVDV clone, capable of serving as a template for transcription into an RNA, wherein said RNA, when introduced into susceptible host cells, induces the generation of infectious BVDV particles:

f) with the capability to induce viraemia and leukopenia in calves for a period of at least one day and at least one of the following clinical symptoms of the group comprising diarrhea and/or pyrexia lasting at least one day when infected with a dose of $6\times10^6 TCID_{50}$; and/or g) with authentical virulence as compared to a wild-type BVDV isolate from which such DNA molecule has been derived; and/or h) which are, when BVDV naive calves aged from 3 to 6 months are infected at a dose of $6\times10^6 TCID_{50}$ with such particles, lethal for at least 30% of such calves within a period of 21 days after infection; and/or i) with a virulence of not less than 90% of BVDV particles comprising an RNA with a sequence complementary to SEQ ID NO:1; and/or j) comprising a sequence complementary to SEQ ID NO:1.

Said dose of $6\times10^6 TCID_{50}$ of step f) is preferably administered as $2\times10^6$ i.m. (gluteal muscle), $2\times10^6$ intranaseally, and $2\times10^6$ subcutaneously (over scapula) to obtain a total dose of $6\times10^6$. Said clinical symptoms of step a) preferably should be observed in at least two thirds of all infected animals. Said leukopenia of step f) preferably shall be at least a 35% reduction below baseline on at least two consecutive days, wherein "baseline" relates to the average values of all animals 10 days before infection.

Said infectious BVDV clone preferably is a type 1 or type 2 clone.

As it is important that said infectious BVDV clone is of authentical virulence, the virus that serves as the origin for constructing such clone is preferably obtained directly from a field isolate or retransferred to animals and subsequently reisolated from the animal with the strongest clinical symptoms and subsequently passaged no more than twice in cell culture, preferably once or not at all. For an illustration example, see Example 1. Example 1 demonstrates the cDNA-cloning of virus NY93/C which is, after several cell culture passages, retransferred into a bovine animal, reisolated and used for RNA preparation and cDNA cloning after not more than two cell culture passages of the reisolated virus.

Another important embodiment of the invention is a BVDV particle generated by transcription using the DNA molecule or the BVDV clone according to the invention into RNA, the transfection of suitable cells or cell lines with said RNA and the collection of the resulting BVDV particles produced by said cells. Yet another embodiment is a BVDV particle generated by cloning the DNA molecule or the BVDV clone according to the invention into the genome of a suitable DNA virus, such DNA viruses being known to the artisan, followed by infection of suitable cells resulting in generation of BVDV particles produced by said cells. Preferably also, the DNA or infectious clone according to the invention may be transfected into suitable cells which then produce the RNA as disclosed for classical swine fever virus (CSFV) by van Gennip, G., et. al. (1999, J. Virol. Methods 78:117–128) for cells which stably express T7 Polymerase. Also preferably the DNA or infectious clone according to the invention may be expressed under control of a eukaryotic promotor in eukaryotic cells leading to the generation of infectious BVDV particles being able to be secreted from the cell (as exemplified by Racaniello, V. R. and Baltimore, D. for poliovirus, 1981, Science 214:916–919).

A highly important embodiment of the invention is an infectious BVDV type 2 clone. Preferably, said infectious BVDV type 2 clone, capable of serving as a template for transcription into an RNA, wherein said RNA, when introduced into susceptible host cells, induces the generation of infectious BVDV particles:

k) with the capability to induce viraemia and leukopenia in calves for a period of at least 1 day and at least one of the following clinical symptoms of the group comprising diarrhea and/or pyrexia lasting at least one day when infected with a dose of $6\times10^6 TCID_{50}$; and/or l) with authentical virulence as compared to a wild-type BVDV isolate from which such DNA molecule has been derived; and/or m) which are, when BVDV naive calves aged from 3 to 6 months are infected at a dose of $6\times10^6 TCID_{50}$ with such particles, lethal for at least 30% of such calves within a period of 21 days after infection; and/or n) with a virulence of not less than 90% of BVDV particles comprising an RNA with a sequence complementary to SEQ ID NO:1; and/or o) comprising a sequence complementary to SEQ ID NO:1.

Preferably, the invention relates to a BVDV type 2 clone obtainable by a method characterized by the following steps:

aaa) a wild-type BVDV type 2 strain is isolated;

bbb) said wild-type BVDV type 2 strain is passaged in cell-culture;

ccc) said cell culture-passaged BVDV type 2 strain is used to infect bovine animals and a BVDV strain is re-isolated from the most severely infected animal;

ddd) said re-isolated BVDV type 2 strain is passaged no more than twice, preferably once, in cell culture;

eee) said re-isolated BVDV type 2 strain is reverse-transcribed and cloned resulting in a full-length cDNA clone, preferably the 5' and 3' ends are cloned using the RACE-technology.

Said infectious DNA clone may then be transcribed into RNA under appropriate conditions, said RNA is introduced into appropriate cells or cell lines and the resulting BVDV type 2 particle is collected. Such a clone is exemplified in the non-limiting Example 1 and characterized by the cDNA sequence SEQ ID NO:1. Thus, a preferred embodiment relates to an infectious BVDV type 2 clone according to the invention as characterized by the DNA sequence of SEQ ID NO:1 or a fragment, functional variant, variant based on the degenerative nucleic acid code, fusion molecule or a chemical derivative thereof. A non-limiting example is provided in Example 1.

The invention further relates to a BVDV type 2 particle generated by in vitro transcription of the BVDV clone according to the invention into RNA, the transfection of suitable cells or cell lines with said RNA and the collection of the resulting BVDV particles produced by said cells. Preferably also, the DNA or infectious clone according to the invention may be transfected into suitable cells which then produce the RNA as disclosed for classical swine fever virus (CSFV) by van Gennip, H. G., et. al., 1999, J. Virol. Methods 78:117–128, for cells which stably express T7 Polymerase. Also preferably the DNA or infectious clone according to the invention may be expressed under control of a eukaryotic promotor in eukaryotic cells leading to the generation of infectious BVDV particles being able to be secreted from the cell (as exemplified by Racaniello, V. R. and Baltimore, D. for poliovirus 1981,Science 214:916–919).

Another highly important aspect of the invention is a DNA molecule containing a nucleotide sequence complementary to a full-length BVDV type 2 RNA. Preferably, said DNA molecule is characterized by the sequence SEQ ID NO:1. Thus, the invention further relates to a DNA molecule according to the invention as characterized by SEQ ID NO:1 or a fragment, functional variant, variant based on the degenerative nucleic acid code, fusion molecule or a chemical derivative thereof. A non-limiting example is provided in Example 1.

Most preferably, the invention relates to a DNA molecule according to the invention, consisting of the sequence comprising SEQ ID NO:1.

The invention further relates to an RNA molecule complementary to the DNA molecule according to the invention as described supra, or to the BVDV clone according to the invention as described supra.

The invention also relates to an RNA molecule obtainable by transcription of the DNA molecule according to the invention as described supra, or the BVDV clone according to the invention as described supra.

Another important aspect of the invention is a method for the production of an infectious BVDV clone from a wild-type BVDV isolate, said infectious BVDV clone being complementary to an RNA having authentical virulence as compared to said wild-type isolate, comprising the steps of:
   p) isolating viral particles from an infected animal; preferably passaging not more than twice on suitable cell culture cells;
   q) preparing RNA from the viral particles;
   r) generating full-length complementary DNA after reverse transcription of the RNA; wherein the reverse transcription includes a step at elevated temperatures sufficient to break or reduce secondary structures of the RNA, and the use of a thermostable enzyme for this step, said enzyme being active at these elevated temperatures;
   s) incorporating the complementary DNA (cDNA) into a plasmid vector or into a DNA virus capable of directing the transcription of BVDV cDNA into RNA upon infection of suitable cells.

Said viral particles preferably are isolated during viremia (step k)). The full length complementary DNA (cDNA) of step m) preferably may be generated by assembling overlapping partial cDNA fragments (see also Example 1).

Another preferred embodiment relates to a method for the production of an infectious BVDV clone from a wild-type BVDV isolate, said infectious BVDV clone being complementary to an RNA having authentical virulence as compared to said wild-type isolate, comprising the steps of:
   ppp) isolating RNA from cells of an infected animal during viraemia or optionally after killing of said animal from its organ(s);
   qqq) generating full-length complementary BVDV DNA which preferably is assembled from DNA fragments after reverse transcription of the RNA; wherein the reverse transcription includes a step at elevated temperatures sufficient to break or reduce secondary structures of the RNA, and the use of a thermostable enzyme for this step, said enzyme being active at these elevated temperatures; and
   rrr) incorporating the complementary DNA (cDNA) into a plasmid vector or into a DNA virus capable of directing the transcription of BVDV cDNA into RNA upon infection of suitable cells.

Suitable cells for cell culture are Madin-Darby bovine kidney (MDBK) cells, RD (bovine testicular) cells or bovine Turbinat (BT) cells. Further suitable cells are known to the person skilled in the art.

The infectious clone produced by the method according to the invention is a type 1 clone or preferably a type 2 clone.

Another important aspect of the invention is a method for the production of an infectious BVDV clone from a wild-type BVDV isolate, said infectious BVDV clone being complementary to an RNA having a virulence of not less than 90% of said wild-type isolate, comprising the steps of:
   t) isolating viral particles from an infected animal;
   u) passaging not more than twice in suitable cell culture cells; preferably once or not at all;
   v) preparing RNA from the viral particles;
   w) generating full-length complementary DNA after reverse transcription of the RNA; wherein the reverse transcription includes a step at elevated temperatures sufficient to break or reduce secondary structures of the RNA, and the use of a thermostable enzyme for this step, said enzyme being active at these elevated temperatures; and
   x) incorporating the complementary DNA (cDNA) into a plasmid vector or into a DNA virus capable of directing the transcription of BVDV cDNA into RNA upon infection of suitable cells.

Said viral particles preferably are isolated during viremia (step t)). The full length complementary DNA (cDNA) of step x) preferably may be generated by assembling overlapping partial cDNA fragments (see also Example 1).

There was a particular difficulty in the art to clone the 5' and 3' region of an infectious BVDV. The inventors developed an inventive method to obtain authentical 5' and 3' regions. Surprisingly, this was possible by applying the RACE-technology. However, only the modification by the inventors of this technique led to the surprising and unexpected generation of BVDV clones of authentic virulence. Preferably, the invention relates to a method according to the invention, wherein the 5' end of the RNA is generated using RACE. Surprisingly, only by applying the RACE technology in conjunction with a thermostable polymerase it was possible to dissolve the secondary structure of the genome successfully.

Standard molecular biology methods are known to the skilled person and can also be found e.g. in Sambrook, S. E., et al.(1989) Molecular Cloning: A Laboratory Manual, $2^{nd}$ ed., Cold Spring Harbor Laboratory Press, Cold Spring Harbor, N.Y. and Bertram, S. and Gassen, H. G. Gentechnische Methoden, G. Fischer Verlag, Stuttgart, New York, 1991).

Preferably, the invention relates to a method according to the invention, wherein RACE is carried out with a thermostable polymerase allowing reaction temperatures of at least 48° C., preferably 50–55° C., preferably also 56–60° C.

Having invented live infectious BVDV particles of defined sequence, the inventors also invented a method to generate attenuated BVDV particles with a defined genetic identity which preferably are attenuated at only one defined genetic marker site. This surprisingly allows the simple determination of revertants or the successful attenuation as only the presence of the genetic marker site needs to be determined by molecular biology methods known to the artisan. XIKE-B and XIKE-C of Example 1 are non-limiting examples for such attenuated BVDV particles of defined sequence.

Another important aspect of the invention is a method of BVD virus attenuation by introducing one or more mutations into the DNA molecule according to the invention as described supra or the infectious BVDV clone as described supra, wherein said mutation or mutations lead to or increase an attenuated phenotype of the recovered BVD virus.

Yet another important aspect of the invention is a method of attenuation of a BVDV strain, comprising the steps of:
  y) introducing one or more mutations into the DNA molecule according to the invention as described supra, or into the infectious BVDV clone according to the invention as described supra;
  z) introducing the mutated DNA into susceptible host cells wherein said DNA is transcribed into RNA or introducing an RNA transcribed from said DNA into said cells; and
  aa) collecting viral particles produced by these cells; wherein said mutation or mutations results in attenuation.

A preferred aspect of the invention is a method of attenuation according to the invention as described supra, wherein the mutation or mutations is a nucleotide substitution, deletion, insertion, addition, or combination thereof.

According to the invention, "mutation" means the replacement of a nucleotide or amino acid by another (e.g. C for a T or histidine for leucine), i.e. a so-called "substitution", or any other mutation such as "deletion" or "insertion". "Deletion" means the removal of one or several nucleotides or amino acids. Insertion means the addition of one or more nucleotides or amino acids.

As these infectious BVDV clones according to the invention are viruses of authentical virulence closely resembling wild-type viruses and at the same time having a defined genotype, said virus must be used as a positive control in animal experiments. Said infectious clones are excellent tools for generating specifically attenuated BVDV clones to be used for e.g. vaccination. The invention comprises BVDV clones wherein the RNase activity residing in glycoprotein $E^{ms}$ is inactivated. Preferably, said RNase activity is inactivated by deletion and/or other mutation such as substitution. Preferably, said deletions and/or other mutations are located at the amino acids at position 295 to 307 and/or position 338 to 357.

Thus, a more preferred aspect of the invention is a method of attenuation according to the invention, wherein the mutation or mutations is in the glycoprotein $E^{ms}$ and causes impairment or loss of function of the mutated protein.

A more preferred aspect of the invention is a method of attenuation according to the invention, wherein the mutation consists of:
  bb) deletion of all or part of the glycoprotein $E^{ms}$; and/or
  cc) deletion or substitution of histidine at position 300 of SEQ ID NO:1; and/or
  dd) deletion or substitution of histidine at position 349 of SEQ ID NO:1.

Most preferably, yet another important embodiment is a method for the attenuation of BVDV, comprising the mutation of a BVDV clone according to the invention at histidine position 300 and/or position 349 wherein the coding triplet in the nucleotide sequence is deleted or substituted.

Yet another important embodiment is a method for the attenuation of BVDV according to the invention, wherein the codon for histidine 300 is substituted by a codon for leucine.

Yet another important embodiment is a method for the attenuation of BVDV according to the invention, wherein the codon for histidine 349 is deleted.

Another important embodiment of the invention is an attenuated BVDV clone or BVDV strain obtainable by a method according to the invention.

Another important embodiment of the invention is a vaccine comprising an attenuated BVDV clone or strain according to the invention, optionally in combination with a pharmaceutically acceptable carrier or excipient.

The invention further relates to the use of an attenuated BVDV clone or strain according to the invention in the manufacture of a vaccine for the prophylaxis and treatment of BVDV infections.

Preferably, a vaccine of the invention refers to a vaccine as defined above, wherein one immunologically active component is a live BVDV, wherein the RNase activity in its protein $E^{ms}$ is inactivated. The term "live vaccine" refers to a vaccine comprising a particle capable of replication, in particular, a replication active viral component.

Preferably, a vaccine according to the invention comprises an attenuated BVD virus type 1 according to the invention combined with an attenuated BVD virus type 2 according to the invention or any other antigenetic group and a pharmaceutically acceptable carrier or excipient. Said vaccine may be administered as a combined vaccine. Most preferably, said attenuated BVD virus type 1 according to the invention may be administered first, followed by an administration of an attenuated BVD virus type 2 according to the invention three to four weeks later.

Preferably, a vaccine according to the invention comprises an attenuated BVD virus type 1 according to the invention wherein the RNase activity in its protein $E^{ms}$ is inactivated, combined with an attenuated BVD virus type 2 according to the invention wherein the RNase activity in its protein $E^{ms}$ is inactivated, or any other antigenetic group wherein the RNase activity in its protein $E^{ms}$ is inactivated, and a pharmaceutically acceptable carrier or excipient. Said vaccine may be administered as a combined vaccine. Most preferably, said attenuated BVD virus type 1 according to the invention as described supra may be administered first, followed by an administration of an attenuated BVD virus type 2 according to the invention as described supra three to four weeks later.

The invention preferably relates to a method of treating a BVDV-infected bovine animal with an attenuated BVDV according to the invention as described supra, wherein said attenuated BVDV or the vaccine composition as disclosed supra is administered to the bovine animal in need thereof at a suitable dose as known to the skilled person and the reduction of BVDV symptoms such as viremia and leukopenia and/or pyrexia and/or diarrhea is monitored. Said treatment preferably may be repeated.

The following examples serve to further illustrate the present invention, but the same should not be construed as limiting the scope of the invention disclosed herein.

EXAMPLE 1

Materials and Methods

Cells and viruses. MDBK cells were obtained from the American Type Culture Collection (Rockville, Md.). Cells were grown in Dulbecco's modified Eagle's medium supplemented with 10% fetal calf serum (FCS; tested for the absence of *pestivirus* and antibodies against *pestiviruses*) and nonessential amino acids. Bovine viral diarrhea strain New York '93 (field isolate VLS#399) was kindly provided by E. J. Dubovi (New York State College of Veterinary Medicine, Cornell University, Ithaca). The virus underwent one animal passage and was designated "New York '93/C" thereafter.

Infection of cells, immunofluorescence assay and virus peroxidase assay. Since pestiviruses are highly associated with their host cells, lysates of infected cells were used for reinfection of culture cells. Lysates were prepared by freezing and thawing cells 3 to 5 days after infection and were stored at −70° C. Unless indicated otherwise in the text, a multiplicity of infection (m.o.i.) of 0,1 was used for infection of culture cells.

For immunofluorescence and peroxidase assays, the infected cells were fixed with ice-cold acetone:methanol (1:1) for 15 min at −20° C., air dried and rehydrated with phosphate buffered saline (PBS). Cells were then incubated with a mixture of anti-BVDV monospecific antibodies directed against E2 (Weiland, E., et al., 1989, J. Virol. Methods 24:237–244). After three washes with PBS, a fluorescein isothiocyanate (FITC)-conjugated rabbit anti-mouse antibody (Dianova, Hamburg, Germany) was used for detecting bound antibodies in the immunofluorescence assays. For peroxidase assays, peroxidase-conjugated goat anti-mouse antibody (Dianova) was used as second antibody. After incubation for one hour at room temperature, cells were washed three times with PBS. Bound antibodies were detected with a solution composed of 50 mM sodium acetate buffer pH 5.0, 1 µM aminoethylcarbazole and 0.1% $H_2O_2$.

Northern (RNA) hybridization. RNA was prepared 48 hours after infection by cesium density gradient centrifugation as described before (Ruimenapf, T., et al. 1989, Virology 171:18–27). Gel electrophoresis, radioactive labelling of the probe, hybridization, and post-hybridization washes were done as described before (Rütmenapf, T., et al. 1989, Virology 171:18–27). A radioactively labelled PCR product (nucleotides 4301 to 5302) from strain New York 93/C was used as a probe.

PCR and RT-PCR. PCR was carried out either with Tfl-Polymerase (Promega, Mannheim, Germany) or with Taq-Polymerase (Appligene, Heidelberg, Germany) following the manufacturer's recommendations and using approximately 50–100 ng of DNA template and 25 pmol of each primer. The sequences of the primers used for amplification of the 5' end of the genome were upstream, $T_{25}V$ primer (Display Systems Biotech, Copenhagen, Denmark); and downstream, CM79: CTCCATGTGCCATGTACAGCAGAG (SEQ ID NO:2) for the first round and CM86: CTCGTCCACATGGCATCTCGAGAC (SEQ ID NO:3) for the nested PCR. The primers used for amplification of the 3' end of the genome were upstream, CM46: GCACTGGTGTCACTCTGTTG (SEQ ID NO:4) for the first round and CM80: GAGAAGGCTGAGGGTGATGCTGATG (SEQ ID NO:5) for the nested PCR and downstream, nls-: GACTTTCCGCTTCTTTTTAGG (SEQ ID NO:6). Reverse transcription PCR (RT-PCR) was was done with the Titan™ One Tube RT-PCR System (Boehringer Mannheim, Germany), using 2 µg of total RNA as a template and following the manufacturer's instructions. The primers for amplification of the $E^{ms}$ coding region were upstream, CM28: GGAGAGAATATCACCCAGTG (SEQ ID NO:7); and downstream, CM21: CTCCACTCCGCAGTATGGACTTGC (SEQ ID NO:8).

The amplified RT-PCR products were purified by preparative agarose gel electrophoresis and elution with the Nucleotrap kit (Macherey-Nagel, Dtiren, Germany) as recommended by the manufacturer.

Phosphorylation and ligation of DNA-oligonucleotides to the 3' ends of RNA. For ligation of a DNA primer to the 3' end of the virus genome, the primer was phosphorylated. 10 µg of the oligonucleotide nls+: CCTAAAAAGAAGCGGAAAGTC (SEQ ID NO:9) were incubated with 5 units of T4 polynucleotide kinase (New England Biolabs, Schwalbach, Germany) in 30 µl kinase-mix (2 mM ATP, 50 mM Tris-HCl pH 7.5, 10 mM $MgCl_2$, 10 mM dithiothreitol, 25 µg/ml bovine serum albumin) for 40 min at 37° C. The primer was passed through a Sephadex G-15 spin column (Sambrook, S. E., et al.(1989) Molecular Cloning: A Laboratory Manual, $2^{nd}$ ed., Cold Spring Harbor Laboratory Press, Cold Spring Harbor, N.Y.) and further purified by phenol/chloroform extraction and ethanol precipitation.

Ligation was carried out using 5 µg of total RNA prepared from infected culture cells and 150 pmol of the phosphorylated oligonucleotide with 20 units of T4-RNA-Ligase (New England Biolabs, Schwalbach, Germany) in 50 µl of ligase-mix (50 mM Tris-HCl pH 7.8, 10 mM $MgCl_2$, 10 mM dithiothreitol, 1 mM ATP, 40% polyethylene glycol and 50 units of RNA guard (Amersham, Freiburg, Germany)) for 16 hours at 17° C. The product was purified by phenol/chloroform extraction and ethanol precipitation.

Synthesis and tailing of single-stranded DNA. Single-stranded (−) DNA from the 5' end of the virus genome was generated with displayThermo-RT reverse transcriptase (Display Systems Biotech, Copenhagen, Denmark) using 2 µg of total RNA from infected cells and 100 pmol of primer CM79 (see "PCR and RT-PCR"), and following the manufacturer's instructions (reaction: 65° C. for 10 min, 42° C. for 40 min, 65° C. for 15 min). The DNA was purified by two sequential phenol/chloroform extractions and ethanol precipitations with ¼ vol of 10 M ammonium acetate (Schaefer, B. C., 1995, Anal. Biochem. 227:255–273).

A poly-dA tail was added to the first cDNA strand with Terminal deoxynucleotidyl Transferase (TdT) (Roche Molecular Biochemicals, Mannheim, Germany) using 50% of the "first strand" product, 50 units terminal transferase, 6.25 µM dATP and 1.5 mM $CoCl_2$ in 50 µl of TdT buffer as recommended by the manufacturer. After incubation at 37° C. for 30 min, the product was purified by phenol/chloroform extraction and ethanol precipitation.

Construction of a cDNA library and nucleotide sequencing. Synthesis of cDNA, cloning and library screening were generally carried out as described previously (Meyers, G., et al. 1991, Virology 180:602–616). cDNA synthesis was primed with oligos BVD13, BVD14 and BVD15 (Meyers, G., et al. 1991, Virology 180:602–616) as well as with B22.1R (GTTGACATGGCATTTTTCGTG) (SEQ ID NO:10), B12.1R (CCTCTTATACGTTCTCACAACG) (SEQ ID NO:11), BVD33 (GCATCCATCATNCCRTGATGAT) (SEQ ID NO:12), N7-3-7 (CAAATCTCTGATCAGTTGTTCCAC) (SEQ ID NO:13), B23-RII (TTGCACACGGCAGGTCC) (SEQ ID NO:14), and B-3' (GTCCCCCGGGGGCTGTTAAGGGTTTTCCTAGTCCA) (SEQ ID NO:15). The probe used for screening the library was the XhoI/AatII insert of a cDNA clone from BVDV strain cp7 (GenBank accession no. U63479, Meyers, G. et al. 1996, J. Virol. 70:8606–8613); hybridisation was carried out at 52° C.

Exonuclease III and nuclease S1 were used to establish deletion libraries of cDNA clones (Henikoff, S., 1987, Methods Enzymol. 155:156–165). Nucleotide sequencing of double-stranded DNA was carried out with the BigDye Terminator Cycle Sequencing Kit (PE Applied Biosystems, Weiterstadt, Germany). As a rule, both DNA strands of the cDNA clones were sequenced; overlaps between independent cDNA clones were sequenced on at least two clones. In total, about 47,000 nucleotides were analyzed which equals an overall coverage of approximately 3.8 for the entire genome. Sequence analysis and alignments were done with Genetics Computer Group software (Devereux, J., et al., 1984, Nucleic Acids Res. 12:387–395).

Construction of the full-length cDNA clone. Restriction, cloning and other standard procedures were generally carried out as described elsewhere (Sambrook, S. E., et al. (1989) Molecular Cloning: A Laboratory Manual, $2^{nd}$ ed., Cold Spring Harbor Laboratory Press, Cold Spring Harbor, N.Y.). Restriction and modifying enzymes were obtained from New England Biolabs (Schwalbach, Germany), Pharmacia (Freiburg, Germany), GibcoBRL (Eggenstein, Germany), and Boehringer Mannheim (Germany).

Five cDNA clones from the library were used for construction of the full-length cDNA clone: plasmid C3/8 (nucleotides 35 to 2411), plasmid C5/11 (nucleotides 22 to 2400) plasmid 8/11 (nucleotides 3400 to 7814), plasmid 13/27 (nucleotides 4783 to 9910) and plasmid C4/24 (nucleotides 8658 to 12322). A fragment "RT-E2" reaching from nucleotide position 2144 to position 4447 was obtained by RT-PCR with primers CM29 (GATGTAGACACATGCGACAAGAACC) (SEQ ID NO:16) and CM51 (GCTTCCACTCTTATGCCTTG) (SEQ ID NO:17), using total RNA from MDBK cells infected with field isolate VLS#399 as a template. In the following description, plasmid restriction sites flanking the viral cDNA inserts are underlined. First, clone C3/8 was cut with AatII and Hindlll, and the cDNA insert was transferred to pACYC 177 cut with the same enzymes. The resulting plasmid was named pKANE5. RT-PCR product "RT-E2" was inserted into the NdeI/HindIII sites of this plasmid after restriction with the same enzymes; the resulting plasmid was pKANE8. Then, the AatII fragment from clone C5/11 was transferred into the AatII site of pKANE8, yielding plasmid pKANE14.

The 5' end of the recombinant cDNA clone was generated by PCR with primers CM87 (GCTCTAGACGGCCGTAATACGACTCACTATAGGTATACGAGA TTAGCTAAAGAACTCGTATATGGATTGGACGTCAAC) (SEQ ID NO:18) that introduces a T7 promoter sequence upstream of the first cDNA nucleotide, and CM79 (see "PCR and RT-PCR"); plasmid C5/11 was used as the PCR template. The PCR product was ligated into the XbaI and BsrGI sites of cDNA clone C5/9, resulting in plasmid pKANE22. Later it was found that oligo CM87 contained a false nucleotide, and pKANE22 was repaired by PCR with oligos CM88 (GACGGCCGTAATACGA CTCACTATAGTATACG)(SEQ ID NO:19) and CM79. The PCR product was treated with *E. coli* DNA-Polymerase I (Klenow fragment) to produce blunt ends and then restricted with BsrGI. It was cloned into the $SpeI^{blunt}$/BsrGI sites of pKANE22, resulting in plasmid pKANE22A.

The insert of cDNA clone 8/11 was cut with Xhol and BamHI and cloned into pACYC177 cut with the same enzymes; the resulting plasmid was named pKANE6. The AvrII/BamHI fragment of cDNA clone 13/27 was transferred to pKANE6, yielding plasmid pKANE15. Then, the EcoRV/MfeI fragment from pKANE14 was inserted into pKANE15 digested with the same enzymes. The resulting plasmid was pKANE21. pKANE21 was digested with SacII and EcoRV, and a corresponding fragment from pKANE14 was cloned into these sites, leading to plasmid pKANE24. Then the SacII/SacII fragment from pKANE 22A was cloned into pKANE24 cut with the same enzyme. The resulting plasmid was pKANE28AII.

The 3' end of the genome was generated by PCR with primers B2-11500 (CCTAACCATGATATATGCCTTCTG) (SEQ ID NO:20) and CM81 (CGGAATTCGCCCGGGCTGTTAGAGGTCTTCCCTAGT) (SEQ ID NO:21) which adds an SrfI site to the 3' end of the genome. The PCR product was cut with BamHI and EcoRI and cloned into pACYC177, resulting in plasmid pKANE17. Then, the ScI/Kpn21 fragment of cDNA clone C4/24 was transferred to pKANE17; the plasmid was called pKANE20. The StuI/EcoRI fragment was excised from pKANE20 and cloned into plasmid pKANE21 which was digested with EcoRI and partially digested with StuI. The resulting plasmid was pKANE23. Finally, the XbaI/PshAI fragment from pKANE28AII was inserted into plasmid pKANE23 cut with the same enzymes, leading to the full-length cDNA clone pKANE40.

Site-directed mutagenesis. All mutants were generated by PCR using the QuikChange site-directed mutagenesis kit (Stratagene, Amsterdam, Netherlands) following the manufacturer's instructions. The plasmid used for introducing mutations into the region coding for $E^{ms}$ was C5/9, a clone obtained from the initial cDNA library (nucleotides 50 to 2411). Oligonucleotides for generating mutant H"346"Δ were CM126 (GAGTGGAATAAAGGTTGGTGTAAC) (SEQ ID NO:22) and CM127 (GTTACACCAACCTTTATTCCACTC) (SEQ ID NO:23), oligos for mutant H"297"L were CM128 (AACAGGAGTCTATTAGGAATTTGGCCA) (SEQ ID NO:24) and CM129 (TGGCCAAATTCCTAATAGACTCCTGTT) (SEQ ID NO:25). The presence of the desired mutations and the absence of second site mutations were verified by nucleotide sequencing.

In Vitro Transcription and RNA Transfection

Transcription of RNA and transfection of MDBK cells were done essentially as described before (Meyers, G. et al. 1996, J. Virol. 70:1588–95). Briefly, 2 g of the respective cDNA construct was linearized with SrfI and purified by phenol extraction and ethanol precipitation. Transcription with T7 RNA polymerase (NEB, Schwalbach, Germany) was carried out in a total volume of 50 µl transcription mix (40 mM Tris-HCl, pH 7.5; 6 mM $MgCl_2$; 2mM spermidine; 10 mM NaCl; 0.5 mM of each ATP, GTP, CTP and UTP; 10 mM dithiothreitol; 100 µg/ml of bovine serum albumine) with 50 units of T7 RNA polymerase in the presence of 15 units RNAguard (Pharmacia, Freiburg, Germany). After incubation at 37° C. for 1 h the reaction mixture was passed through a Sephadex G-50 spun column and further purified by phenol extraction and ethanol precipitation.

If not specified otherwise, transfection was done with a suspension of approximately $3\times10^6$ MDBK cells and about 0.5 µg of in vitro transcribed RNA bound to DEAE-dextran (Pharmacia, Freiburg, Germany). The RNA/DEAE-dextran complex was established by mixing RNA dissolved in 100 µl HBSS (5 g of Hepes, 8 g of NaCl, 0.37 g of KCl, 0.125 g of $Na_2HPO4.2H_2O$ and 1 g of dextrose per Liter; pH 7.05) with 100 µl DEAE-dextran (1 mg/ml in HBSS) and incubation for 30 minutes on ice. Pelleted cells were washed once with DMEM without FCS, centrifuged and then resuspended in the RNA/DEAE-dextran mixture. After 30 minutes incubation at 37° C., 20 µl dimethyl sulfoxide was added and the mixture incubated for 2 minutes at room temperature. After addition of 2 ml HBSS, cells were pelleted and washed once with HBSS and once with medium without FCS. Cells were resuspended in DMEM with FCS and seeded in a 10.0-cm-diameter dish. 48 h to 72 h post transfection cells were split and seeded as appropriate for subsequent analyses.

Electroporation was used for determination of the specific infectivity of RNA. $3 \times 10^6$ MDBK cells in 0.5 ml of phosphate buffered saline (PBS) without magnesium and calcium were mixed with appropriate amounts of RNA and transferred into a 2 mm electroporation cuvette. Electroporation was done with one pulse of 960 µF, 180 Volt in a Hoefer PG 200 Progenetor II. Afterwards, the cells were seeded in 3.5 cm dishes and analyzed by immunofluorescence about 20 h later.

Determination of RNAse activity. MDBK cells were infected with the recombinant viruses and grown for 48 hours. Cells infected with the wild type virus served as a positive control, and uninfected cells were used as a negative control. Cell preparation and measurement of RNase activity were carried out as described before (Meyers, G., et al., 1999, J. Virol. 73:10224–10235) with the exception that incubation of the probes at 37° C. was 30 min instead of 1 hour because longer incubation resulted in considerable background activity in MDBK cells.

Animal experiments. Two animal experiments were carried out to test the recombinant viruses. In the first experiment, two groups of 3 flecked cattle female animals (8 to 10 months old) were inoculated intranasally with $10^5 TCID_{50}$ per animal. In the second experiment, 6 male Holstein and Holstein-cross calves (7 to 10 weeks old) were infected intranasally with $5 \times 10^5 TCID_{50}$ per animal. In the challenge experiment, animals were inoculated with $5 \times 10^6 TCID_{50}$. All animals were tested free of BVDV specific antigen and antibody prior to infection. The different groups were housed in separate isolation units. Clinical parameters were recorded daily as indicated in the results section. Blood was taken from the vena jugularis extema at the time points indicated in the results section and was stabilized with Heparin (about (ca.) 35 I.U./ml) unless it was used for the production of serum.

In order to determine the presence of virus in the blood, buffy coats were prepared from all blood samples. 5 ml ice cold lysis buffer were added to an aliquot of heparin stabilized blood (containing ca. $10^7$ leucocytes) and incubated on ice for 10 min, followed by centrifugation. The pellet was washed once with lysis buffer and twice with PBS without $Ca^{2+}$ and $Mg^{2+}$ before it was resuspended in 2 ml PBS. MDBK cells seeded in 24-well plates were inoculated with 200 µl of the buffy coat preparations and incubated for 5 days. Viral antigen was detected by immunofluorescence microscopy with the BVDV E2 monoclonal antibody (mAb) mix (see above).

The presence of virus-neutralizing antibodies was tested in serum samples that had been inactivated by incubation at 56° C. for 30 min. The sera were diluted in steps of 1:2 on 96 well microtitre plates and inoculated with a suspension of strain New York '93/C/100 TCID50 per well) for 1 hour at 37° C. $10^{1.75}$ MDBK cells were added to each well and incubated for 5 days. Infection was analysed by immunofluorescence, calculated by the method of Kaerber (Mayr, A., et al., 1974, Virologische Arveitsmethoden Bank I. Gustav Fischer Verlag, Stuttgart) and expressed as the 50% endpoint dilution which neutralized approximately 100 $TCID_{50}$.

To detect virus in nasal discharge, nasal swabs were taken at the time points indicated in the results section, diluted in 2 ml of transport buffer (PBS supplemented with 5% FCS, 100 I.U./ml penicillin G, 0.1 mg/ml streptomycin and 2.5 µg/ml amphotericin B) and passed through a 0.2 µm filter. MDBK cells were inoculated in 24 well plates with 100 µl of these preparations and analysed by indirect immunofluorescence microscopy after 5 days.

Results

Genome analysis. The strain NY'93/C is the second BVDV type 2 genome that has been fully sequenced. Northern blot analysis showed that, contrary to strain 890 (Ridpath, J. F. and Bolin, S. R., 1995, Virology 212:39–46), the genome of NY'93/C contains no large insertions or deletions (data not shown). Nucleotide sequence analysis revealed that the genome is 12332 nucleotides long and contains one open reading frame encoding a polyprotein of 3913 amino acids.

The 5' untranslated region (position 1 to 385) was determined by RACE technology and was found to be identical with the New York '93 sequence published by Topliff, C. L. and Kelling, C. L., 1998, Virology 250:164–172 except for position 21. In contrast to other known type 2 genomes (Ridpath, J. F. and Bolin, S. R., 1995, Virology 212:39–46; Topliff, C. L. and Kelling, C. L., 1998, Virology 250: 164–172), strain NY'93/C has adenine at this position instead of thymidine.

Construction and analysis of an infectious cDNA clone for NY'93/C. Although a number of infectious cDNA clones have been established for CSFV and BVDV type 1 (Mendez, E., et al, 1998, J. Virol. 72:4737–4745; Meyers, G., et al. 1996, J. Virol. 70:1588–1595 and 1996, J. Virol 70:8606–8613; Moormann. R. J., et al, 1996, J. Virol. 70:7630770; Vassilev, V. B., et al 1997, J. Virol. 71:471–478; Kuimmerer, B. M. et al, 2000, Vet. Microbiol. 77:117–128), this is the first report of an infectious clone from a BVDV type 2 strain. The clone was designed for runoff transcription with T7 RNA polymerase, resulting in a genome-like RNA without any heterologous additions.

The full-length clone was constituted from four cDNA plasmids selected from the initial phage library and one RT-PCR product encompassing the region between positions 2265 and 4301. At the 5' end, the sequence of the T7 promoter was added for in vitro transcription, and an SrfI site was added to the 3' end for plasmid linearization (FIG. 1). The full-length clone was named pKANE40A.

MDBK cells were transfected with RNA generated from the linearized pKANE40A template by in vitro transcription. A runoff transcript from plasmid pKANE28AII which terminates 19 codons upstream of the NS5B coding region served as a negative control. Three days post transfection, BVDV-specific signals were detected after immunofluorescence staining in cells transfected with RNA from pKANE40A but not in the control. The virus generated from the infectious clone pKANE40A was termed XIKE-A. The transfected cells were passaged twice, and the stock of the second passage was used for all further experiments. The virus was analysed by RT-PCR sequencing, taking the nucleotide exchange from C to T at position 1630 as proof of the identity of XIKE-A.

The specific infectivity of the RNA derived from pKANE40A was determined in comparison to RNA prepared from cells infected with the wild type virus NY'93/C. To this end, the concentration of viral RNA in samples used for transfection of MDBK cells was measured in comparison with defined amounts of the in vitro transcribed RNA after Northern blotting and hybridization, using a phosphoimager. MDBK cells were transfected with similar amounts of both RNAs, and plaques were counted three days post transfection. On the average, the infectivity of RNA derived from pKANE40A was $4.32 \times 10^2$ pfu/µg, and the wild-type RNA yielded $4 \times 10^2$ pfu/µg.

Figure 2:
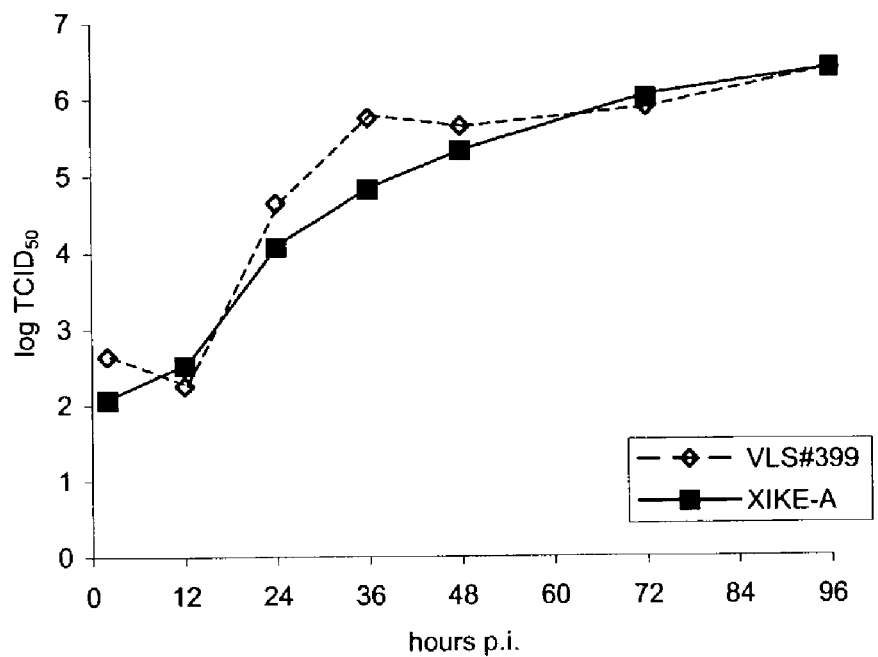
FIG. 2: Growth curves of the recombinant virus XIKE-A and the wild type BVDV isolate VLS#399. MDBK cells were infected with the viruses at an m.o.i of 0.1 and harvested by freezing and thawing at the indicated time points. Titers were determined after infection of new MDBK cells by immunofluorescence staining 72 h p.i.

The growth characteristics of the recombinant virus were analysed through a growth curve, using the original field isolate VLS#399 as a control in the same experiment (FIG. 2). MDBK cells were infected with an m.o.i. of 0.1, and samples were taken at seven time points from 2 hours to 96 hours post infection. The growth curve of the recombinant XIKE-A is somewhat smoother than that of VLS#399, but both viruses reach a titre of $10^{6.39}$ after 96 hours. XIKE-A was therefore deemed suitable for further experiments.

Construction and analysis of $E^{ms}$ mutants. Previous experiments with CSFV (Meyers, G., et al., 1999, J. Virol. 73:10224–10235) had shown that the RNAse activity of the glycoprotein $E^{ms}$ is destroyed by substitution of histidine 297 or 346 (the numbers represent the residue positions in CSFV strain Alfort/Tuibingen) by leucine or lysine, or by deletion of codon "H346". The mutant viruses are viable, but clinically attenuated. In BVDV strain NY'93/C, the two histidine residues are located at position 300 and 349, respectively. To test whether the effects of mutations at these positions would be similar to CSFV in a BVDV type 2 genome, two infectious clones were engineered with either a deletion of codon "H349" or a substitution of codon "H300" by leucine. The resulting recombinant virus mutants were named XIKE-B (H349Δ) and XIKE-C (H300L).

Figure 3:
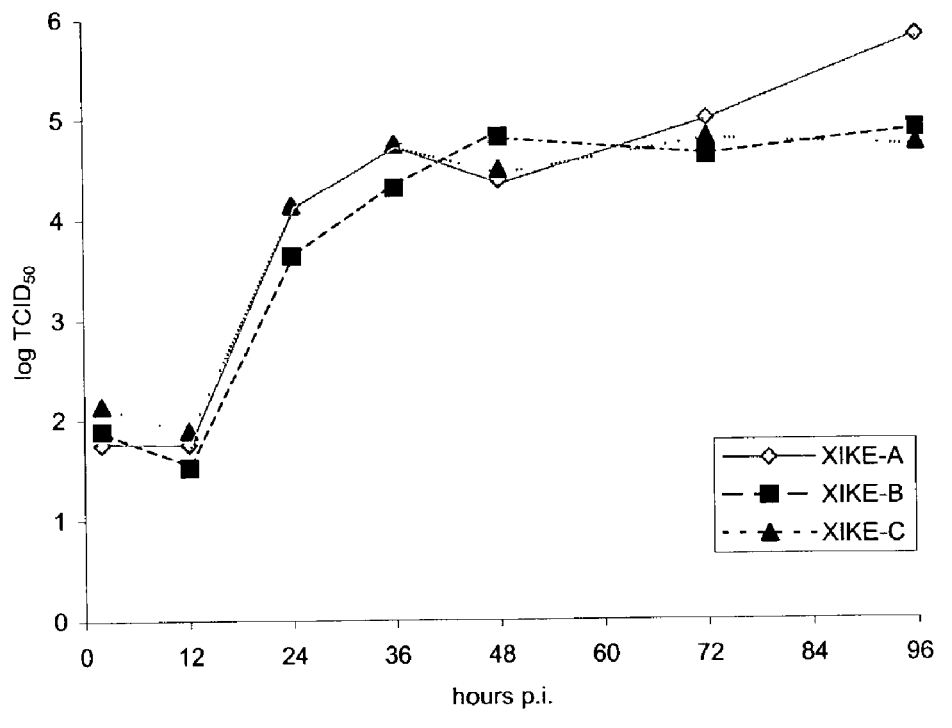

Both mutants were stable in MDBK cells for at least five passages as determined by nucleotide sequencing of RT-PCR products encompassing the $E^{ms}$ coding region. The growth characteristics of the two mutant viruses were compared with virus derived from the wild type infectious clone XIKE-A (FIG. 3).

Figure 4:
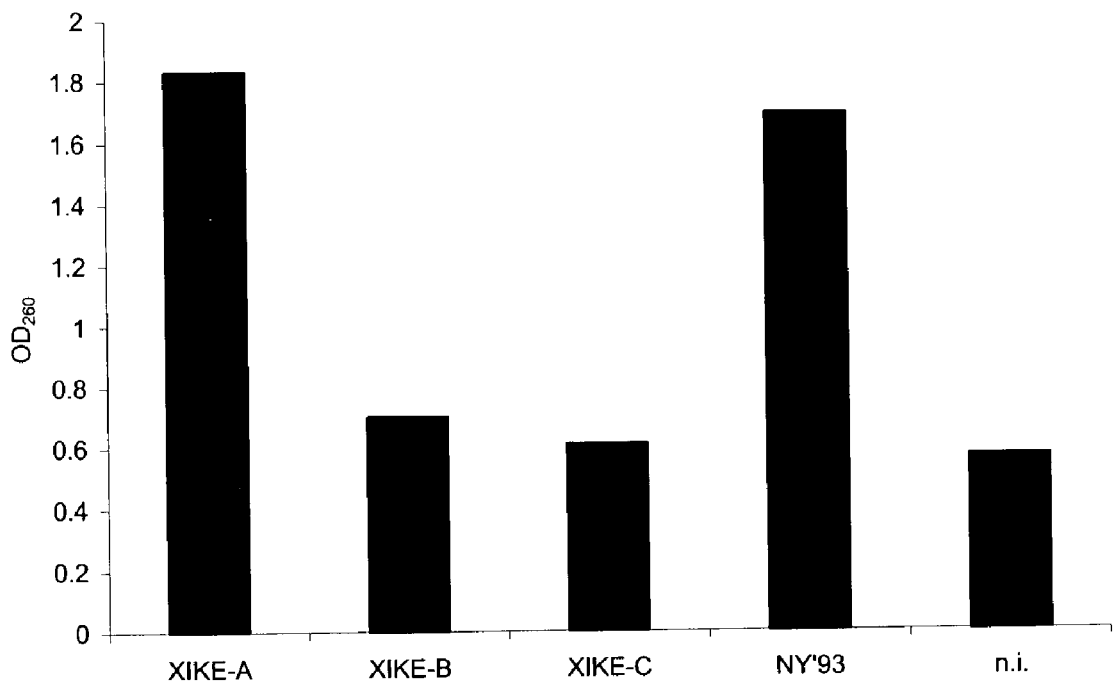
FIG. 4: Determination of RNase activity of the recombinant viruses XIKE-A (wild-type sequence), XIKE-B (H349A) and XIKE-C (H300L) in comparison with the wild type strain New York '93/C from crude cell extracts of MDBK cells infected with the respective viruses. MDBK cells that were not infected served as a negative control (n.i.). The enzymatic degradation of poly(U) was determined by measuring the $OD_{260}$ as a marker of the release of small RNA fragments into the supernatant.

The RNAse activity of XIKE-A, XIKE-B and XIKE-C was determined in crude cell extracts of cells infected with the same m.o.i. of either virus two days post infection. Aliquots of the preparations were tested for their ability to degrade poly(U); cells infected with the wild type strain NY'93/C served as a positive control, and uninfected cells were used as a negative control. After 30 min of incubation, the residual high molecular weight RNA was precipitated, and $OD_{260}$ measurement of the supernatants revealed the presence of small degraded RNA fragments (Meyers, G., et al., 1999, J. Virol. 73:10224–10235). High RNAse activity was found in the NY'93/C and XIKE-A samples whereas the two mutants XIKE-B and XIKE-C were in the same range as the negative control (FIG. 4).

Animal experiment with XIKE-A and NY'93/C. The purpose of the first animal experiment was to compare the virulence and pathogenicity of the recombinant virus XIKE-A derived from the infectious cDNA clone with the wild type strain NY'93/C. Two groups of three animals (8 to 9 months old) were each infected with $10^5 TCID_{50}$ of either XIKE-A (animals #615, #377, #091) or NY'93/C (animals #275, #612, #1610). Each group was housed in a separate isolation unit. Body temperatures and clinical signs were recorded daily; blood samples were taken on days 0, 2 to 16 and 21 p.i. for leukocyte counts and detection of viremia. Sera from all calves were collected for detection of neutralizing antibodies against NY'93/C on days 0, 7, 14, 21, 29 and 35 p.i. Nasal swabs for virus isolation were taken on day 0, 2 to 16 and 21 p.i.

TABLE 1

Virus isolation from buffy coat preparations and nasal swabs of animals infected with New York '93/C or XIKE-A.

| | Virus isolation from buffy coat preparations | | | | | | Virus isolation from nasal swabs | | | | | |
| --- | --- | --- | --- | --- | --- | --- | --- | --- | --- | --- | --- | --- |
| Days p.i. | #275 | #612 | #1610 | | #615 | | #275 | #612 | #1610 | #615 | #377 | #091 |
| −26 | −− | −− | −− | −− | −− | −− | −− | −− | −− | −− | −− | −− |
| 0 | −− | −− | −− | −− | −− | −− | −− | −− | −− | −− | −− | −− |
| 2 | −− | −− | −− | −− | −− | −− | −− | −− | −− | −− | −− | −− |
| 3 | ++ | −− | −− | −+ | ++ | ++ | −− | −− | −− | −− | −− | −− |
| 4 | −+ | ++ | ++ | ++ | ++ | −+ | −− | −− | −− | −− | −− | −− |
| 5 | ++ | ++ | +− | ++ | ++ | ++ | −− | −− | −− | −− | −− | −− |
| 6 | ++ | ++ | ++ | ++ | ++ | ++ | −− | −− | −− | −− | −− | −− |
| 7 | ++ | −+ | ++ | ++ | ++ | ++ | −− | −− | −− | −− | −− | −− |
| 8 | ++ | −− | −− | ++ | ++ | ++ | −− | −− | −− | −− | −− | −− |
| 9 | −− | −− | −− | −− | ++ | −− | ++ | +− | −− | ++ | ++ | ++ |
| 10 | −− | −− | −− | −− | −− | −− | bac | −− | −− | +− | bac | +− |
| 11 | ++ | −− | −− | −− | −− | −− | bac | −− | −− | −− | −− | −− |
| 12 | −− | −− | −− | −− | −− | −− | −− | −− | −− | −− | −− | −− |
| 13 | −− | −− | −− | −− | −− | ++ | −− | −− | −− | −− | −− | −− |
| 14 | −− | −− | −− | −− | −− | * | −− | −− | −− | −− | −− | * |
| 15 | −− | −− | −− | −− | −− | * | −− | −− | −− | −− | −− | * |
| 16 | −− | −− | −− | −− | −− | * | −− | −− | −− | −− | −− | * |
| 21 | −− | −− | −− | −− | −− | * | −− | −− | −− | −− | −− | * |
| total | 7 | 4 | 4 | 6 | 7 | 7 | 1 | 1 | 0 | 2 | 1 | 2 |
| ∅ | | 5 | | | 6, 7 | | | 0, 7 | | | 1, 7 | |

+ virus detected,
− no virus detected,
bac = bacteria,
* animal was euthanized on day 13 p.i.

Figure 5:
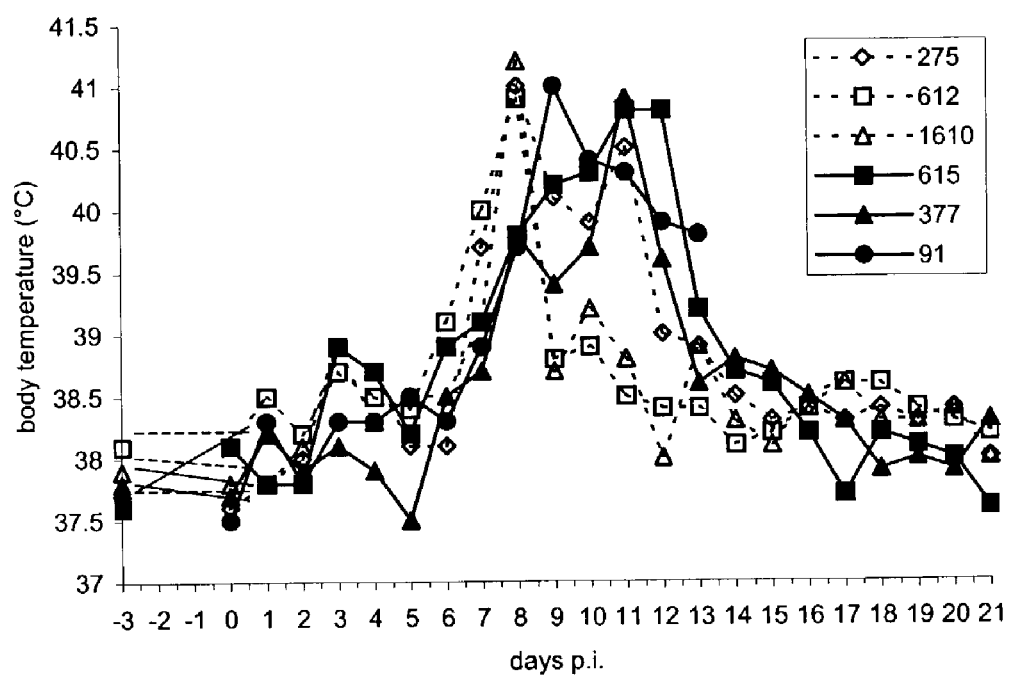
FIG. 5: Body temperatures of animals infected with New York '93/C (animal #275, #612 and #1610, broken lines) or XIKE-A (animal #615, #377 and #091, solid lines).
Figure 6:
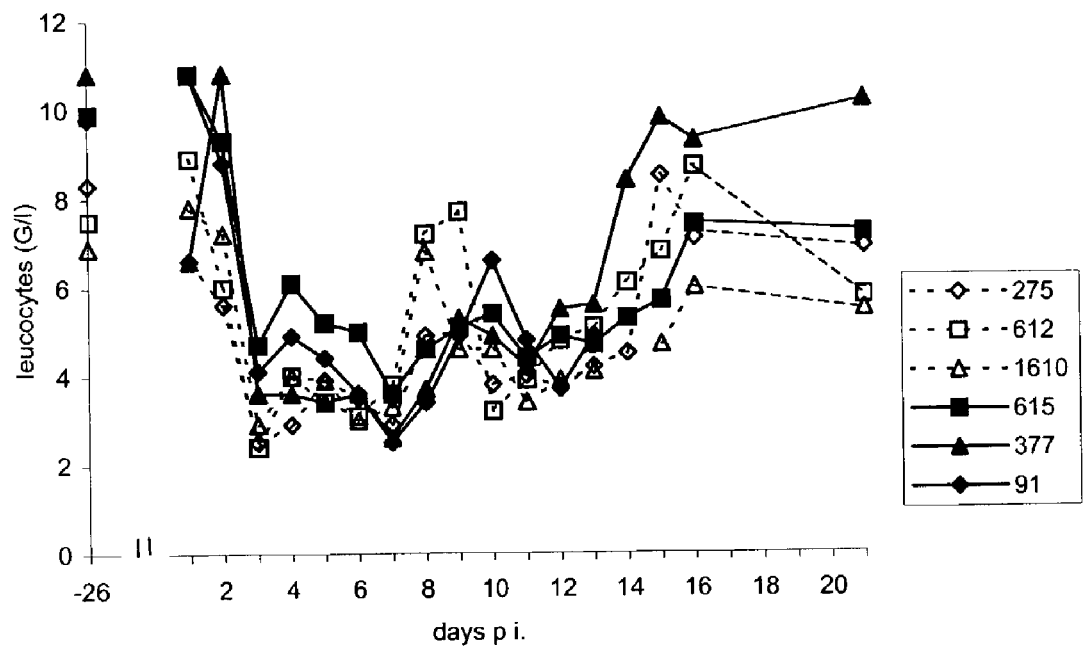
FIG. 6: White blood cell 1 (WBC) counts of animals infected with New York '93/C (animals #275, #612 and #1610, broken lines) or XIKE-A (animals #615, #377 and #091, solid lines).

All animals in both groups developed fever (FIG. 5) and a broad spectrum of clinical signs including respiratory symptoms and gastrointestinal disorders. Animal #091 was killed on day 13 p.i. for welfare reasons. All calves in both groups showed leukopenia starting on day 3 p.i. and persisting for up to day 15 p.i. (FIG. 6). Virus was detected in buffy coat preparations from animals infected with NY'93/C for 5 days, and with XIKE-A for 7 days. Nasal shedding was found for 1 or 2 days (Table 1).

The identity of the viruses was checked by nucleotide sequencing of RT-PCR products from RNA prepared from buffy coat preparations from all animals. The entire $E^{ms}$ coding region (positions 1140 to 1780) was sequenced and found to be identical with the known sequences of NY'93/C or XIKE-A, respectively. Neutralizing antibodies were found in the serum of all calves starting on day 14 p.i. (Table 2).

TABLE 2

Neutralizing antibody titres determined in serum samples of all calves after experimental infection with New York '93/C or XIKE-A. Results are expressed as the reciprocal of the serum BVDV-specific neutralizing antibody titers against New York '93/C ($10^{2.07}$ TCID$_{50}$).

| days p.i. | 615 | 377 | 091 | 275 | 612 | 1610 |
|---|---|---|---|---|---|---|
| −26 | <2 | <2 | <2 | <2 | <2 | <2 |
| 0 | <2 | <2 | <2 | <2 | <2 | <2 |
| 7 | <2 | <2 | <2 | <2 | <2 | <2 |
| 13/14 | 645 | 323 | 406 | 256 | 128 | 40 |
| 21 | 1024 | 1290 | * | 1290 | 512 | 51 |
| 29 | 2580 | 4096 | * | 813 | 2580 | 2580 |
| 35 | 3251 | 3251 | * | 8192 | 2580 | 5161 |

* animal were euthanized on day 13

The results of this study demonstrated that the recombinant virus XIKE-A is highly similar to the wild type virus NY'93/C with regard to both pathogenicity and an the induction of an immune response in the natural host. It is therefore plausbile to assume that any deviation from this clinical picture that might be observed in a virus mutant generated on the basis of the infectious clone pKANE40A would indeed be caused by the desired mutation.

Animal experiment with XIKE-B and XIKE-A. In the second animal experiment, the clinical and immunological characteristics of the RNAse negative mutant XIKE-B were analysed in comparison with XIKE-A. The H349Δ mutant was given precedence over the H300L mutant to minimize the danger of a genomic reversion to wildtype.

Two groups of three calves (7 to 10 weeks old) each were inoculated with a dose of $5 \times 10^5 \text{TCID}_{50}$ of either XIKE-A (animals #387, #388, #418) or XIKE-B virus (animals #415, #417, #419). The groups were housed in separate isolation units. Rectal temperatures and clinical symptoms were monitored daily; nasal swabs and blood samples were taken on days—8, 0, 2 to 14, 17 and 21. Serum samples were collected on days 0, 8, 12/14, 21, 28 and 38/40.

Figure 7:
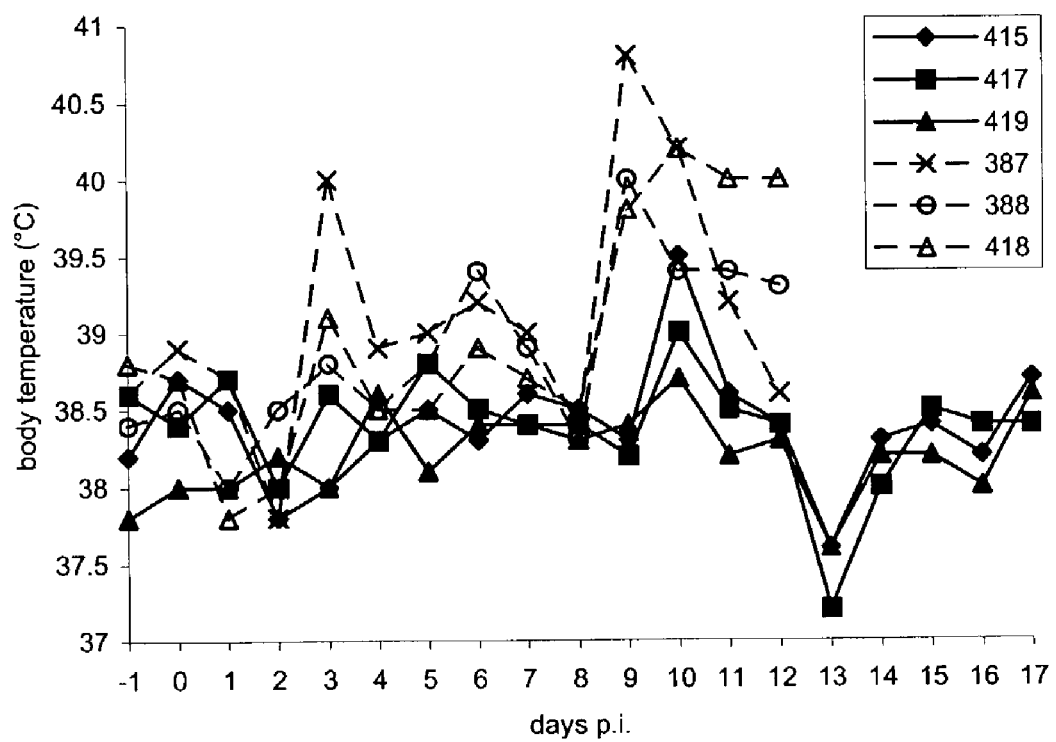
FIG. 7: Body temperatures of animals infected with XIKE-A (animal #387, #388 and #418, broken lines) or XIKE-B (animal #415, #417 and #419, solid lines).
Figure 8:
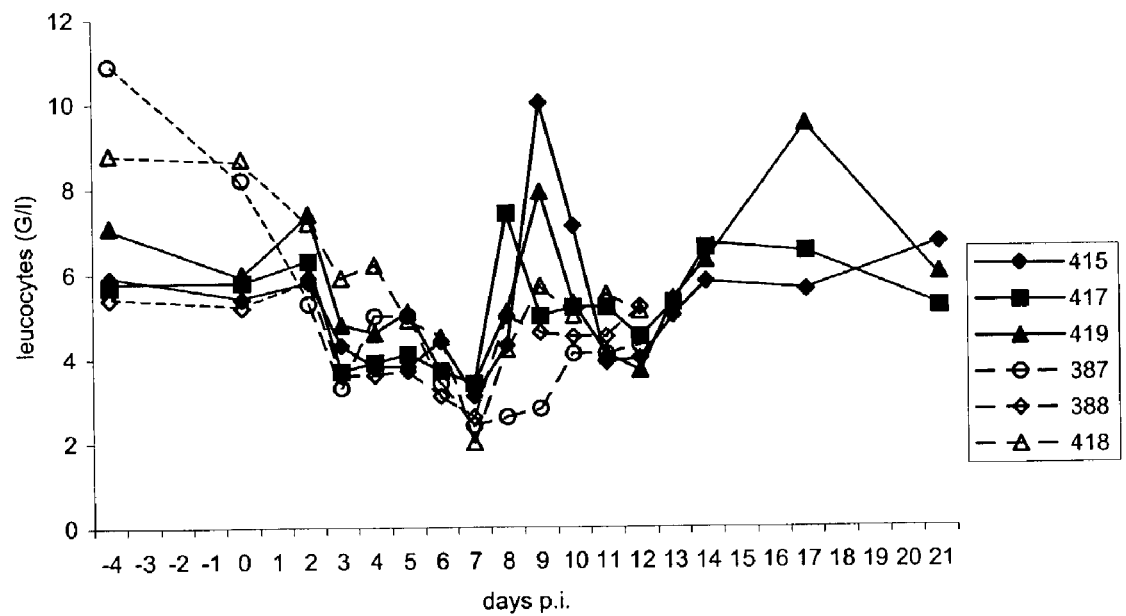
FIG. 8: White blood cell 1 (WBC) counts of animals infected with XIKE-A (animals #387, #388 and #418, broken lines) or XIKE-B (animals #415, #417 and #419, solid lines).

Nine to ten days post infection, the calves infected with XIKE-A developed fever for up to 3 days; in addition animal #387 had fever on day 3 p.l. (FIG. 7) that was accompanied by diarrhea and respiratory symptoms. Calf #388 showed convulsions. The group was euthanized for welfare reasons on day 12 p.i. in a state of marked depression and anorexia. None of the calves infected with XIKE-B had elevated body temperatures (FIG. 7). Only mild respiratory symptoms were observed for up to 6 days. Leukopenia was found in all animals; however, the decrease of leucocyte numbers was more pronounced in the calves infected with wild type XIKE-A than in the XIKE-B group (FIG. 8).

Virus was found in buffy coat preparations of all animals starting on day 4 p.i.; however, viremia was shorter for the $E^{ms}$ mutant (about 4 days) than for the virus with wild type sequence (about 8 days). Nasal shedding of virus could be observed for up to 8 days (about 4,7) with XIKE-A animals, but for a maximum of 1 day (about 0,7) with XIKE-B animals (Table 3).

TABLE 3

Virus isolation from buffy coat preparations and nasal swabs of animals infected with the recombinant virus XIKE-A (animals #387, #388 and #418) or the $E^{ms}$ mutant XIKE-B (animals #415, #417 and #419).

| | Virus isolation from buffy coat preparations | | | | | | Virus isolation from nasal swabs | | | | | |
|---|---|---|---|---|---|---|---|---|---|---|---|---|
| Days p.i. | #415 | #417 | #419 | #387 | #388 | #418 | #415 | #417 | #419 | #387 | #388 | #418 |
| −8 | -- | -- | -- | -- | -- | -- | -- | -- | -- | -- | -- | -- |
| 0 | -- | -- | -- | -- | -- | -- | -- | -- | -- | -- | -- | -- |
| 2 | -- | -- | -- | -- | -- | -- | -- | -- | -- | -- | -- | -- |
| 3 | -- | -- | -- | -- | -- | -- | -- | -- | -- | -- | -- | -- |
| 4 | +- | +- | -- | ++ | ++ | ++ | -- | -- | -- | -- | -- | -- |
| 5 | ++ | +- | +- | ++ | ++ | ++ | -- | -- | -- | -- | -- | +- |
| 6 | ++ | +- | ++ | ++ | ++ | ++ | -- | +- | -- | -- | -- | +- |
| 7 | ++ | ++ | ++ | ++ | ++ | ++ | -- | -- | +- | +- | -- | +- |
| 8 | -- | +- | -- | ++ | ++ | ++ | -- | -- | -- | -- | -- | +- |
| 9 | -- | -- | -- | ++ | +- | ++ | -- | -- | -- | ++ | ++ | +- |
| 10 | -- | -- | -- | ++ | +- | +- | -- | -- | -- | +- | +- | ++ |
| 11 | -- | -- | -- | ++ | +- | ++ | -- | -- | -- | +- | -- | +- |
| 12 | -- | -- | -- | -- | -- | -- | -- | -- | -- | -- | -- | ++ |
| 13 | -- | -- | -- | * | * | * | -- | -- | -- | * | * | * |
| 14 | -- | -- | -- | * | * | * | -- | -- | -- | * | * | * |
| 17 | -- | -- | -- | * | * | * | -- | -- | -- | * | * | * |
| 21 | | | | * | * | * | | | | * | * | * |
| total | 4 | 5 | 3 | 8 | 8 | 8 | 0 | 1 | 1 | 4 | 2 | 8 |
| Ø | | 4 | | | 8 | | | 0,7 | | | 4,7 | |

+ virus detected,
− no virus detected,
* animals were euthanized on day 12 p.i.

Again, nucleotide sequencing of RT-PCR products encompassing the entire E$^{ms}$ coding region was used for virus identification in buffy coat preparations. As expected, isolates from animals #387, #388 and #418 were wild type. A deletion of the "H349" codon was confirmed for animals #415, #417 and #419. Interestingly, an additional point mutation was found in RT-PCR products from two of these animals (#415 and #419): nucleotide position 1246 was changed from guanine to thymine, resulting in the amino acid substitution Q287H. Neutralizing antibodies were first detected on day 12 p.i. in the serum of the calves infected with XIKE-A, and on day 14 p.i. in the serum of calves infected with the E$^{ms}$ mutant (Table 4).

TABLE 4

Neutralizing antibody titres determined in serum samples of all calves after experimental infection with XIKE-A (wild type sequence) or XIKE-B (H346?). Results are expressed as the reciprocal of the serum BVDV-specific neutralizing antibody titers against New York '93/C ($10^{1.7}$ TCID$_{50}$).

| days p.i. | 387 | 388 | 418 | 415 | 417 | 419 |
|---|---|---|---|---|---|---|
| 0 | <2 | <2 | <2 | <2 | <2 | <2 |
| 8 | <2 | <2 | <2 | <2 | <2 | <2 |
| 12/14 | 20 | 8 | 128 | 51 | 203 | 64 |
| 21 | * | * | * | 512 | 1024 | 406 |
| 28 | * | * | * | 2048 | 1024 | 4096 |
| 38/40 | * | * | * | 8182 | 4096 | 4096 |

* animals were euthanized on day 12

EXAMPLE 2

Experimental Design

Twelve pregnant heifers were selected from a BVDV negative herd. The following group of 5/7 heifers were included in the trial:

| | No. | Inoculation | Virus |
|---|---|---|---|
| Group 1: | 5 | One i. n. administration, 3 ml in each nostril | XIKE-A |
| Group 2: | 5 | One i. n. administration, 3 ml in each nostril | NY-93 |

Heifers were moved to the experimental facilities 8 days before inoculations. Pregnancy status was confirmed after transport into the experimental facility. Heifers were between days 60 and 90 of gestation on the day of inoculation. Inoculation took place for all animals at one point of time with $2.5 \times 10^4$ TCID$_{50}$/ml of the respective virus applied in 6 ml tissue culture supernatant.

Heifers were monitored for the presence of clinical signs of BVDV infection including abortions during the observation period. The experiment was terminated 9 weeks after infection. Non-aborted cows were slaughtered, the uterus examined and collected. Foetal organ samples were collected during routine necropsy and examined for BVDV infection.

The presence of fetal infection was the main evaluation parameter, composed from the number of BVDV-related cow mortality, the number of BVDV-related abortions and the number of BVD positive fetuses at termination.

Results:

| Animal No. | Conclusion |
|---|---|
| Group 1 | |
| 526 | BVD abortion |
| 598 | BVD abortion |
| 615 | BVD abortion |
| 618 | BVD abortion |
| 626 | Heifer Died due to BVD |
| Group 2 | |
| 184 | Heifer Died due to BVD |
| 203 | BVD abortion |
| 232 | Heifer Died due to BVD |
| 233 | Foetus BVD positiv (viremic) |
| 252 | BVD abortion |
| 267 | Heifer died due to BVD |
| 306 | BVD abortion |

EXAMPLE 3

This study aimed to assess the efficacy of BVDV isolates against foetal infection. Efficacy of the NY93 infectious copy derivative BVDV recombinant (type II) with a deletion of the RNase function in the E(RNS) protein XIKE-B (H349Δ) is investigated to prevent fetal infection after an heterologous type I challenge.

Between day 60 and 90 is the most sensitive period for fetal exposure to BVDV. Therefore in this trial heifers derived from BVDV-free farm (and confirmed seronegative for BVDV) have been immunized by a single exposure with XIKE B (i.m.). Thereafter heifers were inseminated and between day 60–90 animals, when animals are supposed to be highly sensitive to BVDV fetal infection, a challenge infection with a wild type field virus was performed. The intranasal route for challenge was chosen as this mimics the normal route of infection in the field best.

Experimental Design:

Heifers were selected from a BVDV negative herd. The heifers were tested serologically and virologically negative for BVDV. The following groups of heifers were included in the trial:

| | | Challenge | No. of heifers: | |
|---|---|---|---|---|
| Group | Treatment | BVDV | Vaccinated | Challenged |
| 1 | None | Type I | NA | 2 |
| 2 | Isolate XIKE-B | Type I | 10 | 4 |

Group 1 remained untreated in the herd of origin until challenge. Blood samples were collected post-vaccination for buffy coat preparation and serology.

Inseminations started 4 weeks after immunisation for all groups. Group 1 was transported to the experimental facility before challenge.

Heifers were challenged 4 months and 10 days after vaccination. At the day of inoculation, pregnancy status was between day 60 and 90 of pregnancy.

The prevention of foetal infection was the main evaluation parameter.

Sequence of Events and Time Schedule

| | |
|---|---|
| Immunisation | 10 days after transport to the animal facility |
| Insemination | In a period of 30 days, started approximately 4 weeks after immunisation |
| Second transport to the challenge facility | At least 10 days before challenge |
| Challenge | Between day 60 to 90 of pregnancy |
| Observations | Continuous for about 2 months |
| Slaughter of animals and harvest of foetuses for virus isolation testing of fetal organ samples | About 2 months post-challenge |

BVDV Challenge Viruses

The virus is grown in BVDV free medium as appropriate, aliquoted and frozen at −70° C. [±10 C.].

| | |
|---|---|
| Type/designation:: | Type I/ncp KE#9 |
| Passage level: | 4 |
| Composition: | Isolate obtained from German field |

| | |
|---|---|
| Challenge dose: | $10^5$ per animal |
| Applied volume: | 6 ml per animal (3 ml per nostril) |
| Inoculation route: | Intranasal |

Vaccinations

The vaccination schedule is described in the Experimental Design Section.

| | |
|---|---|
| Description: | XIKE-B, live virus BVDV strain |
| Passage number: | 10 |
| Virus dose: | $10^5$ per animal |
| Applied vaccine volume: | 2 ml per animal |
| Application route: | Intramuscular (i.m.) |

Results:

Rectal Temperatures

The temperature values were below 39° C. in all but one cases, and no unusual fluctions were seen during the observation period. Heifer No. 1249 (Group 1) had a temperature of 39.1° C. on 14 DPI (=days post infection) that returned to normal value on the next day.

Leukocyte Counts

DPI values of zero (0) were considered as individual baseline for comparison. No lower limit of leukocyte counts was defined in the study protocol. However, a reduction of leukocyte counts by 40% or more, i.e., values reaching 60% of the baseline value (established on the day of challenge) or lower, was considered biologically significant.

Indivdual mean leukocyte counts are shown in Table 5 below.

TABLE 5

| | Individual mean leukocyte counts | | | | | | | | | | | | | | |
|---|---|---|---|---|---|---|---|---|---|---|---|---|---|---|---|
| ID | Days post infection (DPI) | | | | | | | | | | | | | | |
| No. | 0* | 2 | 4 | 6 | 8 | 10 | 12 | 14 | 16 | 18 | 20 | 22 | 24 | 26 | 28 | 30 |
| | Group 1 | | | | | | | | | | | | | | | |
| 1249 | 11,2 | 12,3 | 4,9 | 6,3 | 6,6 | 12,8 | 11,3 | 10,4 | 9,6 | 8,6 | 11,2 | 12,2 | 12,0 | 11,8 | 10,4 | 7,5 |
| 1126 | 10,0 | 8,3 | 5,1 | 6,1 | 5,5 | 13,2 | 14,2 | 11,0 | 11,7 | 8,9 | 12,6 | 11,4 | 9,9 | 11,9 | 12,4 | 8,3 |
| | Group 2 | | | | | | | | | | | | | | | |
| 1200 | 13,2 | 13,1 | 15,2 | 14,8 | 17,3 | 13,7 | 16,5 | 12,8 | 10,6 | 11,5 | 13,3 | 13,2 | 13,8 | 11,2 | 10,1 | 11,8 |
| 1217 | 9,4 | 8,0 | 9,4 | 14,3 | 10,4 | 11,1 | 15,0 | 10,4 | 8,1 | 8,2 | 12,7 | 10,8 | 11,8 | 10,3 | 12,2 | 8,0 |
| 1197 | 11,3 | 11,1 | 12,5 | 11,8 | 8,4 | 11,7 | 9,0 | 6,1 | 8,5 | 8,8 | 9,5 | 12,2 | 12,1 | 9,1 | 9,8 | 8,5 |
| 1214 | 8,9 | 9,4 | 9,2 | 10,2 | 12,8 | 7,5 | 10,6 | 7,7 | 7,6 | 11,1 | 10,7 | 10,9 | 8,8 | 9,1 | 7,8 | 10,2 |

*0 day samples were collected on the day before infection

Baseline leukocyte counts were similar in all groups. While both heifers in Group 1 (infected with Type I strain) experienced a biologically significant reduction in leukocyte counts (values highlighted with grey colour) after the challenge (maximum drop noted 4–8 DPI), the corresponding vaccinated heifers (Group 2) had no remarkable falls in leukocytes. The only exception was heifer No. 1197 who showed a significant decrease on a single day, on Day 14 PI. On the very next day, leukocyte count returned to what was considered normal (less than 40% deviation from baseline).

Virus Isolation Data

Methods applied for virus isolation investigations are detailed in previous examples. Virus isolation data from buffy coats (described as day post infection (=DPI) with vaccine candidate (XIKE B):

| Group | Animal ID | 0 DPI | 2 DPI | 4 DPI | 6 DPI | 8 DPI | 10 DPI | 12 DPI | 14 DPI | 16 DPI | 18 DPI | 20 DPI | 22 DPI | 24 DPI | 26 DPI | 28 DPI | 30 DPI |
|---|---|---|---|---|---|---|---|---|---|---|---|---|---|---|---|---|---|
| 1 | 1126 | − | − | + | + | + | + | − | + | + | − | − | − | − | − | − | − |
| 1 | 1249 | − | − | − | − | + | + | − | − | − | − | − | − | − | − | − | − |
| 2 | 1197 | − | − | − | − | − | − | − | − | − | − | − | − | − | − | − | − |
| 2 | 1200 | − | − | − | − | − | − | − | − | − | − | − | − | − | − | − | − |
| 2 | 1214 | − | − | − | − | − | − | − | − | − | − | − | − | − | − | − | − |
| 2 | 1217 | − | − | − | − | − | − | − | − | − | − | − | − | − | − | − | − |

Virus isolation from fetal organs:

| Group | Animal ID | Mesenteric lymphnodes | Small intestine | Spleen | Thymus | kidney | Sternum bone marrow | Cerebellum | placenta |
|---|---|---|---|---|---|---|---|---|---|
| 1 | 1126 | + | + | + | + | + | + | + | + |
| 1 | 1249 | + | + | + | + | + | + | + | + |
| 2 | 1197 | − | − | − | − | − | − | − | − |
| 2 | 1200 | − | − | − | − | − | − | − | − |
| 2 | 1214 | − | − | − | − | − | − | − | − |
| 2 | 1217 | − | − | − | − | − | − | − | − |

All heifers did not show any clinical symptoms typical for BVDV infection after vaccination with XIKE B. After challenge heifers of group 1 had on at least one day viremia, whereas in group 2 on no day after challenge viremia could be detected. All fetuses from heifers of group 1 were positive for BVDV (all of the following organs were positive tested for BVDV by virus isolation (mesenteric lymph nodes; small intestine, spleen, thymus, kidney, sternum, bone marrow, cerebellum); the fetuses from from heifers of group 2 were all negative (in all tested organs consistently: mesenteric lymph nodes; small intestine, spleen, thymus, kidney, sternum, bone marrow, cerebellum) for BVDV.

Therefore infectious copy derived virus was attenuated successfully and the potential of the use as vaccine virus in order to prevent fetal infection was shown.

The XIKE B virus belongs antigenetically to the BVDV type 2 viruses and is effective in preventing fetal infection after challenge with an heterologous challenge virus belonging to the BVDV type 1 antigenic group.

What is claimed is:

1. An isolated DNA molecule containing a nucleotide sequence selected from the group consisting of
   (a) a full-length SEQ ID NO. 1, and
   (b) a full-length variant of SEQ ID NO. 1, based on the degenerative nature of the genetic code,
wherein the isolated DNA molecule can be used to generate an attenuated BVDV type 2 clone effective in preventing fetal infection after challenge with a heterologous challenge virus of the BVDV type 1 antigenic group.

2. An isolated infectious BVDV clone, capable of serving as a template for transcription into an RNA, wherein the RNA, when introduced into susceptible host cells, induces the generation of infectious BVDV particles and wherein the RNA sequence is complementary to a nucleotide sequence selected from the group consisting of
   (a) a full-length SEQ ID NO. 1, and
   (b) a full-length variant of SEQ ID NO. 1, based on the degenerative nature of the genetic code,
wherein the isolated DNA molecule can be used to generate an attenuated BVDV type 2 clone effective in preventing fetal infection after challenge with a heterologous challenge virus of the BVDV type 1 antigenic group.

3. A BVDV particle generated by transcribing the DNA molecule according to claim 1 or the BVDV clone according to claim 2.

4. The DNA molecule according to claim 1, wherein the nucleotide sequence comprises SEQ ID NO. 1.

5. A method of preventing fetal infection after challenge with a heterologous virus of the BVDV type 1 antigenic group in an animal in need thereof comprising administering to the animal an attenuated BVDV type 2 clone generated from an isolated DNA molecule containing a nucleotide sequence selected from the group consisting of
   (a) a full-length SEQ ID NO. 1, and
   (b) a full-length variant of SEQ ID NO. 1, based on the degenerative nucleic acid code.

* * * * *

SEQUENCE LISTING

<160> NUMBER OF SEQ ID NOS: 25

<210> SEQ ID NO 1
<211> LENGTH: 12332
<212> TYPE: DNA
<213> ORGANISM: ORGANISM:  Bovine viral diarrhea virus (BVDV)

<400> SEQUENCE: 1

```
gtatacgaga ttagctaaag aactcgtata tggattggac gtcaacaaat ttttaattgg        60
caacgtaggg aaccttcccc tcagcgaagg ccgaaaagag gctagccatg cccttagtag       120
gactagcaaa agtaggggac tagcggtagc agtgagttcg ttggatggcc gaaccccctga      180
gtacagggga gtcgtcaatg gttcgacact ccattagtcg aggagtctcg agatgccatg       240
tggacgaggg catgcccacg gcacatctta acccatgcgg gggttgcatg ggtgaaagcg       300
ctattcgtgg cgttatggac acagcctgat agggtgtagc agagacctgc tattccgcta       360
gtaaaaactc tgctgtacat ggcacatgga gttgttttca aatgaacttt tatacaaaac       420
atataaacaa aaaccagcag gcgtcgtgga acctgtttac gacgtcaacg ggcgcccact       480
gtttggagag agcagtgact tgcacccgca gtcaacacta aaactaccac accaacgagg       540
cagcgccaac atcctgacca atgctaggtc cctaccgcgg aaaggtgact gccggagagg       600
taatgtgtat ggaccggtga gtggcatcta tatcaaacca ggaccgatct actaccagga       660
ttatgtgggc cccgtctatc atagagcccc actggaacta tgtagggagg caagtatgtg       720
cgaaacaact aggagagttg gcagagtgac cggtagtgat gggaaattat atcatatcta       780
catctgcata gatgggtgta tcctcctgaa gagggcgact aggaaccaac agaagtcct        840
gaaatgggta tacaacagat taaattgtcc tttatgggtc accagctgct ccgatgaagg       900
gagcaagggt gctacaagta agaagcagcc taagccagat aggatagaaa aggtaagat        960
gaaaatagcc ccaaaagaga cagaaaaaga ttgcaaaacc agacccccg acgcgactat       1020
agtagtagaa ggggttaagt accaggtgaa gaaaaaagga aggtaaggg gaaaaaatac       1080
tcaagatggg ttatatcaca acaagaataa gcccctgaa tcaagaaaaa aattggaaaa       1140
ggcactgctg gcttgggcca tcttagcagc ggtcctgctt cagctggtaa caggagagaa       1200
tatcacccag tggaacttga tggacaacgc accgaggga atacagcaag cgatgttcct       1260
aagagggggtg aacaggagtc tacatggaat ttggccagag aaaatttgca ccggagtacc       1320
aactcactta gcaacagact atgagcttaa agagatagtg gggatgatgg acgcgagtga       1380
gaagaccaac tacacgtgtt gcaggttgca aagacatgag tggaataaac atggttggtg       1440
taactggttt catatagaac cgtggatatg gttgatgaac aaaacccaaa acaacctgac       1500
agaagggcaa ccgcttaggg agtgtgctgt gacttgtagg tatgacaagg aaacagaatt       1560
gaacatcgtg acacaggcta gggacagacc tacaactctg acaggttgca agaaaggcaa       1620
gaatttctct ttcgcaggtg ttatactgga tgggccctgt aactttaaag tatcggttga       1680
agatgtgctg ttcaaggagc acgattgcgg caacatgctg caagagaccg cgatacagct       1740
actcgatggg gcaaccaaca ccattgaggg agcaagggta gggacggcca agttgacaac       1800
ctggttaggg aagcaattag ggatccttgg taagaagttg gagaacaaaa gcaaagcatg       1860
gtttggtgca catgcagcaa gtccatactg cggagtggag aggaagatcg gttacgtatg       1920
gtatacaaaa aactgcactc cagcttgcct tccaagaaac actagaataa taggccccgg       1980
gaaatttgat accaacgccg aagatggaaa aatactccat gagatggggg ggcacctctc       2040
agaatttgtc ctattgtcct tggtggttct gtctgacttt gccccggaaa ccgcgagcgt       2100
catctacttg gttctacatt ttgcgatccc gcaaagccac gttgatgtag acacatgcga       2160
caagaaccag ctgaatttaa cggtagcaac cacagtagca gaggtcatac cagggacagt       2220
gtggaaccta gggaagtatg tctgcataag accagactgg tggccatatg agacgacgac       2280
```

-continued

| | |
|---|---|
| agtcttcgtc atagaggaag cagggcaagt aatcaaattg atgctaaggg ccatcagaga | 2340 |
| cttaactagg atatggaatg ctgccactac cacagctttc ttaatctttt tagtaaaagc | 2400 |
| actgagggga caactaatcc aagggctatt gtggctgatg ctaataacag gagcacaggg | 2460 |
| cttccctgaa tgcaaagagg gcttccaata tgccatatct aaagacagga aaatggggtt | 2520 |
| attgggccca gagagcttaa ctacaacatg gcacctcccc accaaaaaaa tagtggattc | 2580 |
| catggtgcat gtatggtgtg aaggaaaaga cttgaaaata ttaaaaatgt gcacaaagga | 2640 |
| agagaggtat ctagtggctg tgcacgagag agccttatca accagtgccg agtttatgca | 2700 |
| gatcagtgat gggacaatag gcccagacgt gatagatatg cctgatgact ttgagtttgg | 2760 |
| actctgccct tgtgactcaa aaccagtgat aaagggcaaa tttaatgcca gcttactgaa | 2820 |
| tggaccagct ttccagatgg tatgcccaca ggggtggact ggtacaatag aatgcaccct | 2880 |
| agcgaaccaa gacaccttgg acacaactgt cattaggaca tatagaagaa ctaccccatt | 2940 |
| tcagcggaga aaatggtgta cctatgaaaa aataataggg gaagatatct atgaatgcat | 3000 |
| tctaggtgga aactggacat gcataaccgg tgaccatagc aggttgaaag acggacctat | 3060 |
| caagaagtgt aagtggtgtg ccatgactt cgtcaactca gagggctac cacactaccc | 3120 |
| aataggcaag tgcatgctca tcaacgagag tgggtacagg tatgtagatg cacctcttg | 3180 |
| cgatagggt ggtgtagcca tagttccatc tggcaccgta aagtgtagaa taggtaacgt | 3240 |
| cacggtgcaa gttatcgcta ctaacaatga tctgggaccc atgccttgca gcccagctga | 3300 |
| agtgatagca agtgaaggac cagtggaaaa gactgcatgc acattcaact attcaaggac | 3360 |
| tctacctaat aagtattatg agccaaggga ccggtacttc caacaataca tgttaaaagg | 3420 |
| ggagtggcaa tattggttcg acctggattc tgtagaccac cacaaagact acttctcaga | 3480 |
| gttcataatc atagcagtgg tcgccttgtt gggtggtaag tacgtactgt ggctcttgat | 3540 |
| aacatacaca atactgtctg agcagatggc tatgggtgct ggagtgaata ctgaagagat | 3600 |
| agtcatgata ggcaatttgc tgacagacag tgatattgag gttgtggttt atttccttct | 3660 |
| tctgtactta atagttaaag aggaactggc gaggaaatgg attatactgg tataccacat | 3720 |
| ccttgtagcc aaccctatga aaacaattgg ggtcgtctta ctaatgctag ggggagtggt | 3780 |
| gaaggccagc agaatcaatg ctgatgacca aagtgctatg gacccatgct tcttctcgt | 3840 |
| gacaggcgta gtggctgttt tgatgatcgc tagaagagaa cctgccacat taccactgat | 3900 |
| tgtagcattg ctagcaataa gaacatcagg attcctactg cccgctagca ttgatgtaac | 3960 |
| tgtagcagta gtattaattg tactttgtt ggctagctac ataacagact actttagata | 4020 |
| taaaaagtgg cttcaactct tatttagtct gatagctggt atctttatta taaggagctt | 4080 |
| aaaacatatc aaccagatgg aggtaccaga atatctatg ccaagttgga gacctctagc | 4140 |
| tctggtcctt ttctatataa catctacagc aataaccact aattgggaca ttgacttagc | 4200 |
| aggcttcctg ctgcaatggg cgccagcagt gatcatgatg gctaccatgt gggcagactt | 4260 |
| tttgactctg atcatagtcc tgcccagtta cgagttatct aagctttact tcctaaagaa | 4320 |
| cgtcaggaca gacgtggaaa agaactggct cggcaaagtg aaatacagac agatcagttc | 4380 |
| agtttatgac atctgtgaca gtgaggaagc agtgtaccta tttccatcaa ggcataagag | 4440 |
| tggaagcagg ccagatttca tattccctt tttgaaagcc gtgttaataa gctgcatcag | 4500 |
| cagccaatgg caagtggttt acatttctta cctaatactg gaaattacat actatatgca | 4560 |
| caggaaaatc atagatgagg tgtcaggagg agcaaatttt ctatcaagac tcatagcagc | 4620 |
| catcatagaa ttaaattggg ccatagatga tgaggaatgt aaaggactga agaaactgta | 4680 |

-continued

```
tctcttgtca gggagagcga agaatttgat agttaaacat aaggtaagaa atgaagccgt   4740
ccacagatgg tttggtgagg aggaaatata cggggcaccc aaggtgatca ctatcataaa   4800
agctagtacc ctaagtaaaa acaggcactg cataatctgc acgatctgtg aagggaaaga   4860
atggaatgga gccaactgcc caaagtgtgg aagacaagga aagcccataa catgtggaat   4920
gacactcgca gactttgagg agaaacatta caaaaagata tttataagag aagaatcttc   4980
ttgtcctgtg ccttttgatc cttcttgcca ttgtaattat tttcgccacg atgggccttt   5040
caggaaagag tataagggtt acgtccaata cacagccaga ggacaactct ttctgaggaa   5100
cctaccaatt ctagcgacga agatgaagct attaatggtg ggaaacctcg gcgcagaaat   5160
tggcgacctg aacatctag gatgggtact gagagggcca gccgtgtgca aaaaaattac   5220
caaccatgag aagtgccacg taaacatcat ggataagcta actgcatttt ttggaatcat   5280
gcctagaggc acgacccta gggcacctgt gaggttcccc acagcactac taaaagtgag   5340
aaggggcta gagacgggat gggcttacac gcaccaagga gggatcagct cggtagacca   5400
tgtcacagcc ggaaaggatt tactagtgtg tgacagtatg ggcaggacca gggttgtctg   5460
tcatagtaac aataagatga ctgatgagac tgagtatggc atcaagaccg actcagggtg   5520
tcccgaaggt gcgaggtgtt acgtgctaaa cccagaagct gttaacattt ctggcacaaa   5580
aggagctatg gtacacctcc agaaaacggg gggggagttc acatgtgtca ctgcctcagg   5640
gacccccggct ttcttcgatc tgaaaaatct aaaaggctgg tccgggctac caattttga   5700
agcatccagt ggcagggtgg ttggtagggt gaaagtcggc aagaatgagg attccaagcc   5760
caccaaacta atgagcggaa tccagacagt gtctaagaac cagacagacc tagcggacat   5820
cgtaaaaaaa ttgactagta tgaacagagg agagttcaaa cagataacat tagccactgg   5880
ggcaggaaaa actacggaac tgccaaggtc cgtcatagag gagatagggaa ggcacaaaag   5940
ggtcttagtc ctgataccat tgagagcagc agcagagtca gtgtatcagt atatgagagt   6000
gaagtacc ca agtatatctt tcaatttgag aataggagat atgaaggaag gtgacatggc   6060
cactggtatc acctacgcct catatgggta cttttgtcag cttcctcagc ccaaactgag   6120
agctgccatg gtagagtact catatatatt cttagatgag taccactgtg ctacacccga   6180
gcaattagca ataattggaa agatacacag gtttgctgaa atcttagag tggtagcaat   6240
gacagcaacc ccagctggaa cggtcacaac gactggtcag aaacaccta tagaggagtt   6300
catagcccca gaggtgatga aagtgaaga tctaggtagt gaatacttgg atattgcagg   6360
gttgaagata ccgactgaag agatgaaagg caacatgctc gtgttcgcgc caactaggaa   6420
catggcagta gaaacagcta agaaattgaa ggctaaggga tacaactctg gatactatta   6480
cagtgggga a accccagaga acttgagggt ggtaacctcg caatcccgt atgtggtagt   6540
agccaccaat gccatagagt caggtgtgac attaccagac ttagacacag ttgtagacac   6600
tggactaag tgtgagaaga gggtgaggat ttcttcaaaaa atgcccttca ttgtaacagg   6660
acttaagaga atggcagtca caatcggaga gcaagcccag cgcagggta gagtaggaag   6720
agtcaagcca ggtaggtact ataggagtca agaaacagct tcagggtcaa aagattacca   6780
ttacgaccta ctgcaagccc agaggtacg aatagaagat ggaattaatg taacaaagtc   6840
attcagggag atgaactatg attggagcct ttacgaagag gacagcttga tgataactca   6900
actcgaggtc cttaacaacc tccttatatc agaagacctg cctgccgcag tgaagaacat   6960
catggccggg accgatcacc cagaacccat acaactggcc tataacagtt atgaaaaacca   7020
```

```
aattccagtg ctgttcccaa agatcaaaaa tggtgaggtg acagacagtt atgagaatta    7080
cacatatctc aatgcaagaa aattaggaga ggacgtgccg gcatatgtgt acgccacaga    7140
ggatgaggat ctagcagtgg atcttctggg tatggattgg ccggacccag gcaaccaaca    7200
ggtggtagag acagggaggg cattaaaaca agtaactggc ttatccacag cagaaaacgc    7260
cctcttgata gccctattcg gctacgtcgg gtaccagaca cttcaaaaa ggcacatacc     7320 catgattact gacatctata cacttgaaga ccacaggctt gaggacacaa cccacctcca    7380
gtttgcccca aacgctataa ggaccgacgg caaggactca gagttgaagg aattagctgt    7440
gggagacctt gataaatatg tggacgcact ggtagactac tccaaacaag ggatgaaatt    7500
catcaaagtc caagctgaaa aggtcagaga ctcccagtct acgaaggaag cttgcaaac    7560 cattaaggag tatgtggata agtttataca atcactaaca gagaataagg aggagatcat    7620
caggtatgga ctatggggag ttcacacggc actctacaaa agcttggcag cgagactggg    7680
gcatgaaaca gcttttgcaa ctttagtggt aaaatggttg gcttttgggg cgaaacggt     7740 atctgctcac atcaagcaag tagcagttga tctagtagta tattatatca tcaacaaacc    7800
atcttttcct ggagatacag agacccaaca agaggggagg aagtttgtgg ctagtctttt    7860
tatatctgca ctagcaacat acacatataa aacctggaat tacaacaatc tgcaacgggt    7920
tgtcgaacct gccttagctt acctcccata tgctacaagt gccttgaagt tgttcacacc    7980
cacaagatta gagagtgtgg tcatactcag ttctacaatt tacaagacat acctctctat    8040
aaggaagggt aagagtgacg gcttgttagg tacaggcata agtgcagcca tggagatctt    8100
aaaccaaaac ccaatctcag taggtatatc tgtgatgctg ggggtaggtg ccatcgccgc    8160
ccataatgca atagaatcta gtgaacagaa aagaactttg ctgatgaagg tctttgtaaa    8220
aaacttctta gaccaagcag caacagatga gctagtcaaa gagaaccctg aaaaaataat    8280
catggctcta tttgaagcag tccagaccat aggaaacccc ctaagactca tctaccatct    8340 gtacgggtg tactataagg ggtgggaagc aaaagaactc gcagagaaaa ctgctggccg      8400
caacttattc acattgatca tgtttgaggc ctttgagctt ttaggtatgg actcagaagg    8460
aaagataaga aacttgtcag gcaactacat actggactta atcttcaact tgcataataa    8520
attaaacaag gggctcaaaa aactagtcct tgggtgggct cctgcacctt tgagctgtga    8580
ttggacacca agtgatgaga gaataagcct acctcataac aactacttaa gggtagaaac    8640
caggtgtcct tgtggctatg agatgaaggc aataaaaaat gttgctggta aattgacaaa    8700
agttgaagaa aaggggtcct tcctatgcag gaatagatta gggagaggac ctccaaactt    8760
caaagtaaca aagttctatg atgataactt gatagaagtc aagccagtag ctaggctaga    8820
aggccaggtg gacctctatt acaagggagt aacagctaag ttagactaca caatgggaa     8880 agtactgtta gctaccaaca gtgggaggt ggaccacgct ttcctgacca gactagtaaa     8940
gaagcacaca gggataggtt ttaaaggtgc atatttgggt gaccgaccag accatcaaga    9000
tcttgtcgat agagattgtg caactataac gaagaactca gtacagttcc taaaaatgaa    9060
gaagggttgc gctttcacat atgacctaac aatctctaac cttgtcaggc ttattgaact    9120
agtccataag aataattact aagaaagaga gatccctacc gtgacagtaa ctacttggct    9180
tgcatattct tttgtcaatg aagacctggg gactatcaag cctgtattgg gggagaaagt    9240
catcccagaa cccccgagg agttgagtct ccaacccacc gtgagactag tcaccactga     9300
aacagcaata accataacag gggaggctga agtgatgacg acaggatca caccagtggt     9360 agagatgaaa gaagaacctc agctggacca ccagtcaact accctaaagg tagggttgaa    9420
```

```
ggaaggggaa tatccagggc caggagttaa ccctaaccat ttagcagagg tgatagatga    9480
gaaagatgac aggccttttg tcctaatcat cggtaacaaa ggttctacct cgaacagagc    9540
aagaacggcc aagaatatac ggctgtacaa aggaaacaac ccaagagaga tcagggatct    9600
gatgagccaa ggaagaatat tgacggttgc tctaaaagag ttggacccgg aattaaaaga    9660
attagtagat tacaagggga cctttctcaa tagggaagct ttagaagccc taagcttagg    9720
taagccaatc aagaggaaaa ccacaacagc aatgatcagg aggttaatag agccagaggt    9780
tgaggaggaa ctaccagatt ggttccaagc ggaagaaccc ctattttgg aagcaaaaat     9840
acagaatgac ttataccacc taattggcag tgtagatagt ataaaagca aagcaaagga     9900
attaggggcc acagataaca caaagatagt gaaggaagtt ggggctagga cctatacgat    9960
gaaattgagc agctggagca cacaagttac aaaaaaacag atgagtctag cccctctctt   10020
tgaagagctg ttattaaagt gccctccatg tagtaaaatt tcaaagggac atatggtgtc   10080
agcataccaa ctggctcaag gaaactggga acccctcggg tgtgggtct  atatgggaac   10140
cataccagct aggcgtctca agatccaccc ttatgaggct taccttaaac tcaaagagct   10200
ggtggaagtt gaatcttcga gggccactgc aaaagaatcc atcataagag aacataacac   10260
ctggatcctg cggaaggtga gacatgaagg gaacctaaga accaaatcaa tgatcaaccc   10320
tgggaaaata tcagatcagc tatgcagaga tggacacaaa agaaacatat ataataagat   10380
cataggctca acaatggcct ctgctggtat taggctggag aaactgccag tagtccgagc   10440
ccaaactgac acaccagtt tccaccaagc cataagagaa aaaattgata aaacagaaaa    10500
caagcagacc cctgaattgc atgaagaact aatgaaggtc ttcgactgct taaagatccc   10560
agagctgaag gaatcgtatg atgaagtttc atgggaacaa ttagaagccg ggataaaccg   10620
taagggtgca gcaggctatc tagagagcaa gaacataggg gaagtcctag acacagagaa   10680
acacatagta gagcagctga tcaaggatct gaggaagggg aagaagatta ggtactatga   10740
aacagccatc cccaagaatg agaagagaga cgtcagcgac gactgggaag ccggagagtt   10800
cgttgatgaa aagaaaccaa gagtaatcca gtacccggac gccaaggtga gactggccat   10860
tacaaaagtg atgtacaaat gggtaaagca aaaaccagtg gtgatacccg gctatgaagg   10920
taaaacacct ctatttgaca tattcaacaa agtgaagaag gaatgggatt cattccagga   10980
ccccgtagca gtgagctttg acaccaaagc gtgggataca caagtcacca gtagagacct   11040
aatgttgata aaggatatcc agaaatatta tttcaagaga agtatacaca aattttttaga  11100
tacaataaca gaacacatgg tggaggtacc tgtcattaca gcagacggtg aagtttacat   11160
aaggaatggt cagaggggta gtggccaacc cgacacaagt gctggtaata gtatgttgaa   11220
tgtcctaacc atgatatatg ctttctgtaa aagtacaggc ataccttaca ggggattcag   11280
cagagtggca agaatccatg tgtgtggtga tgatggcttt ttgataacag agagaggact   11340
gggactgaaa ttctctgaga agggtatgca agatattacat gaggccggga agccccagaa  11400
aataactgaa ggggacaaaa tgaaagtggc atacagattc gaggacatag agttttgttc   11460
ccatactccc gtgccagtca gatgggcaga taacaccagt agttacatgg cagggaggag   11520
cacagccact atactagcta agatggcaac caggctggat ccagcggag agaggggtag    11580
cacagcttat gagaaggccg tagccttcag cttcctttg atgtactcat ggaatcccgt    11640
agttagaagg atctgcttac tggtgttgtc acagtttcca gaaatatccc catccaaaaa   11700
cacaatatac tactaccaag gggatcccat agctgcgtac agagaagtga tagggaaaca   11760
```

```
gctgtgtgaa ctgaaaagaa caggatttga gaagctggct ggtctgaatt tgagtatgac    11820
cactctaggc atctggacaa acatactag taaaagacta atccaagcct gtgtagaaat    11880
aggtaagaga gaaggtacct ggttagttaa tgctgacaga ctgattgcag gaaagactgg    11940
gaagttttac atcccaagca ctggtgtcac tctgttggga aaacactatg aggaaattaa    12000
cttaaagcaa aaggcggcac aaccgccgat agaggggtt gacagatata agttgggccc    12060
catagttaat gttatcttga gaaggctgag ggtgatgctg atgacagttg ccagcggaag    12120
ctggtgaatc cgtccggagc gtcgtgccct cactcaaggt ttttaattgt aaatattgta    12180
aatagacagc taagatattt attgtagttg gatagtaatg cagtgatagt aaatacccca    12240
atttaacact acctccaatg cactaagcac tttagctgtg tgaggttaac tcgacgtcca    12300
cggttggact agggaagacc tctaacagcc cc                                 12332

<210> SEQ ID NO 2
<211> LENGTH: 24
<212> TYPE: DNA
<213> ORGANISM: Artificial Sequence
<220> FEATURE:
<223> OTHER INFORMATION: PCR Primer

<400> SEQUENCE: 2
ctccatgtgc catgtacagc agag                                          24

<210> SEQ ID NO 3
<211> LENGTH: 24
<212> TYPE: DNA
<213> ORGANISM: Artificial Sequence
<220> FEATURE:
<223> OTHER INFORMATION: PCR Primer

<400> SEQUENCE: 3
ctcgtccaca tggcatctcg agac                                          24

<210> SEQ ID NO 4
<211> LENGTH: 20
<212> TYPE: DNA
<213> ORGANISM: Artificial Sequence
<220> FEATURE:
<223> OTHER INFORMATION: PCR Primer

<400> SEQUENCE: 4
gcactggtgt cactctgttg                                               20

<210> SEQ ID NO 5
<211> LENGTH: 25
<212> TYPE: DNA
<213> ORGANISM: Artificial Sequence
<220> FEATURE:
<223> OTHER INFORMATION: PCR Primer

<400> SEQUENCE: 5
gagaaggctg agggtgatgc tgatg                                         25

<210> SEQ ID NO 6
<211> LENGTH: 21
<212> TYPE: DNA
<213> ORGANISM: Artificial Sequence
<220> FEATURE:
<223> OTHER INFORMATION: PCR Primer

<400> SEQUENCE: 6
gactttccgc ttcttttag g                                              21
```

<210> SEQ ID NO 7
<211> LENGTH: 20
<212> TYPE: DNA
<213> ORGANISM: Artificial Sequence
<220> FEATURE:
<223> OTHER INFORMATION: PCR Primer

<400> SEQUENCE: 7
ggagagaata tcacccagtg                                               20

<210> SEQ ID NO 8
<211> LENGTH: 24
<212> TYPE: DNA
<213> ORGANISM: Artificial Sequence
<220> FEATURE:
<223> OTHER INFORMATION: PCR Primer

<400> SEQUENCE: 8
ctccactccg cagtatggac ttgc                                          24

<210> SEQ ID NO 9
<211> LENGTH: 21
<212> TYPE: DNA
<213> ORGANISM: Artificial Sequence
<220> FEATURE:
<223> OTHER INFORMATION: oligonucleotide

<400> SEQUENCE: 9
cctaaaaaga agcggaaagt c                                             21

<210> SEQ ID NO 10
<211> LENGTH: 21
<212> TYPE: DNA
<213> ORGANISM: Artificial Sequence
<220> FEATURE:
<223> OTHER INFORMATION: oligonucleotide

<400> SEQUENCE: 10
gttgacatgg cattttcgt g                                              21

<210> SEQ ID NO 11
<211> LENGTH: 22
<212> TYPE: DNA
<213> ORGANISM: Artificial Sequence
<220> FEATURE:
<223> OTHER INFORMATION: oligonucleotide

<400> SEQUENCE: 11
cctcttatac gttctcacaa cg                                            22

<210> SEQ ID NO 12
<211> LENGTH: 22
<212> TYPE: DNA
<213> ORGANISM: Artificial Sequence
<220> FEATURE:
<221> NAME/KEY: variation
<222> LOCATION: 12
<223> OTHER INFORMATION: n=a or g or c or t
<220> FEATURE:
<221> NAME/KEY: variation
<222> LOCATION: 15
<223> OTHER INFORMATION: n=g or a

<400> SEQUENCE: 12
gcatccatca tnccntgatg at                                            22

<210> SEQ ID NO 13
<211> LENGTH: 24
<212> TYPE: DNA
<213> ORGANISM: Artificial Sequence
<220> FEATURE:
<223> OTHER INFORMATION: oligonucleotide

<400> SEQUENCE: 13
caaatctctg atcagttgtt ccac                                           24

<210> SEQ ID NO 14
<211> LENGTH: 17
<212> TYPE: DNA
<213> ORGANISM: Artificial Sequence
<220> FEATURE:
<223> OTHER INFORMATION: oligonucleotide

<400> SEQUENCE: 14
ttgcacacgg caggtcc                                                    17

<210> SEQ ID NO 15
<211> LENGTH: 35
<212> TYPE: DNA
<213> ORGANISM: Artificial Sequence
<220> FEATURE:
<223> OTHER INFORMATION: oligonucleotide

<400> SEQUENCE: 15
gtcccccggg ggctgttaag ggttttccta gtcca                                35

<210> SEQ ID NO 16
<211> LENGTH: 25
<212> TYPE: DNA
<213> ORGANISM: Artificial Sequence
<220> FEATURE:
<223> OTHER INFORMATION: PCR Primer

<400> SEQUENCE: 16
gatgtagaca catgcgacaa gaacc                                           25

<210> SEQ ID NO 17
<211> LENGTH: 20
<212> TYPE: DNA
<213> ORGANISM: Artificial Sequence
<220> FEATURE:
<223> OTHER INFORMATION: PCR Primer

<400> SEQUENCE: 17
gcttccactc ttatgccttg                                                 20

<210> SEQ ID NO 18
<211> LENGTH: 78
<212> TYPE: DNA
<213> ORGANISM: Artificial Sequence
<220> FEATURE:
<223> OTHER INFORMATION: PCR Primer

<400> SEQUENCE: 18
gctctagacg gccgtaatac gactcactat aggtatacga gattagctaa agaactcgta     60
tatggattgg acgtcaac                                                   78

<210> SEQ ID NO 19
<211> LENGTH: 32
<212> TYPE: DNA
<213> ORGANISM: Artificial Sequence

```
<220> FEATURE:
<223> OTHER INFORMATION: PCR Primer

<400> SEQUENCE: 19
gacggccgta atacgactca ctatagtata cg                              32

<210> SEQ ID NO 20
<211> LENGTH: 24
<212> TYPE: DNA
<213> ORGANISM: Artificial Sequence
<220> FEATURE:
<223> OTHER INFORMATION: PCR Primer

<400> SEQUENCE: 20
cctaaccatg atatatgcct tctg                                       24

<210> SEQ ID NO 21
<211> LENGTH: 36
<212> TYPE: DNA
<213> ORGANISM: Artificial Sequence
<220> FEATURE:
<223> OTHER INFORMATION: PCR Primer

<400> SEQUENCE: 21
cggaattcgc ccgggctgtt agaggtcttc cctagt                          36

<210> SEQ ID NO 22
<211> LENGTH: 24
<212> TYPE: DNA
<213> ORGANISM: Artificial Sequence
<220> FEATURE:
<223> OTHER INFORMATION: oligonucleotide

<400> SEQUENCE: 22
gagtggaata aaggttggtg taac                                       24

<210> SEQ ID NO 23
<211> LENGTH: 24
<212> TYPE: DNA
<213> ORGANISM: Artificial Sequence
<220> FEATURE:
<223> OTHER INFORMATION: oligonucleotide

<400> SEQUENCE: 23
gttacaccaa cctttattcc actc                                       24

<210> SEQ ID NO 24
<211> LENGTH: 27
<212> TYPE: DNA
<213> ORGANISM: Artificial Sequence
<220> FEATURE:
<223> OTHER INFORMATION: oligonucleotide

<400> SEQUENCE: 24
aacaggagtc tattaggaat ttggcca                                    27

<210> SEQ ID NO 25
<211> LENGTH: 27
<212> TYPE: DNA
<213> ORGANISM: Artificial Sequence
<220> FEATURE:
<223> OTHER INFORMATION: oligonucleotide

<400> SEQUENCE: 25
tggccaaatt cctaatagac tcctgtt                                    27
```